US012350021B2

(12) United States Patent
Cheng et al.

(10) Patent No.: US 12,350,021 B2
(45) Date of Patent: *Jul. 8, 2025

(54) NON-BAROMETRIC DETERMINATION OF HEMODYNAMIC EFFECTS OF CARDIAC ARRHYTHMIAS USING SIGNALS SENSED BY AN IMPLANTABLE DEVICE

(71) Applicant: Chelak Medical Solutions Inc, Houston, TX (US)

(72) Inventors: Jie Cheng, Houston, TX (US); Dhanunjaya Lakkireddy, Houston, TX (US)

(73) Assignee: Chelak Medical Solutions Inc, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/410,888

(22) Filed: Jan. 11, 2024

(65) Prior Publication Data

US 2024/0260842 A1      Aug. 8, 2024

Related U.S. Application Data

(63) Continuation of application No. 16/532,112, filed on Aug. 5, 2019, now Pat. No. 11,903,683.

(Continued)

(51) Int. Cl.
*A61B 5/00* (2006.01)
*A61B 5/02* (2006.01)
(Continued)

(52) U.S. Cl.
CPC ........ *A61B 5/02055* (2013.01); *A61B 5/0084* (2013.01); *A61B 5/02028* (2013.01);
(Continued)

(58) Field of Classification Search
None
See application file for complete search history.

(56) References Cited

U.S. PATENT DOCUMENTS 7,925,335 B2    4/2011    Feldman et al.
8,075,498 B2   12/2011    Leo et al.
(Continued)

FOREIGN PATENT DOCUMENTS

DE           19836496        2/2000
WO      WO2014143387 A1     9/2014
(Continued)

OTHER PUBLICATIONS

Flockhart et al., "Two-axis bend measurement with Bragg gratings in multicore optical fiber", Optics Letters, Mar. 15, 2003, Optical Society of America, US, vol. 28, Nr: 6, p. 387.

(Continued)

*Primary Examiner* — John R Downey
*Assistant Examiner* — Anant A Gupta
(74) *Attorney, Agent, or Firm* — Dority & Manning, P.A.

(57) ABSTRACT

Certain aspects of the present disclosure provide methods, apparatus, and computer-readable media for determining hemodynamic stability in a subject. In one example method, an optical signal is transmitted via at least one optical fiber in a set of one or more optical fibers partially disposed in a heart of the subject, wherein the at least one optical fiber in the set is configured to bend with the mechanical movement of the heart. A reflected portion of the optical signal is received via the at least one optical fiber, wherein changes in at least one parameter of the received reflected portion of the optical signal are indicative of the mechanical movement of the heart. A hemodynamic stability of the heart is determined based on the received reflected portion. Hemodynamic stability of the subject may further be determined (Continued)

based on thermal, ultrasound, and/or impedance signals measured in or near the heart.

14 Claims, 8 Drawing Sheets

Related U.S. Application Data

(60) Provisional application No. 62/714,217, filed on Aug. 3, 2018.

(51) Int. Cl.
| | |
|---|---|
| *A61B 5/0205* | (2006.01) |
| *A61B 5/287* | (2021.01) |
| *A61B 5/349* | (2021.01) |
| *A61B 8/08* | (2006.01) |
| *A61B 8/12* | (2006.01) |
| *A61N 1/39* | (2006.01) |
| *A61B 5/0215* | (2006.01) |

(52) U.S. Cl.
CPC .............. *A61B 5/287* (2021.01); *A61B 5/349* (2021.01); *A61B 5/686* (2013.01); *A61B 5/6869* (2013.01); *A61B 8/0883* (2013.01); *A61B 8/12* (2013.01); *A61N 1/3956* (2013.01); *A61B 5/02154* (2013.01)

(56) References Cited

U.S. PATENT DOCUMENTS

| | | |
|---|---|---|
| 8,706,219 B2 | 4/2014 | Feldman et al. |
| 8,929,976 B2 | 1/2015 | Feldman et al. |
| 8,932,288 B2 | 1/2015 | Leo et al. |
| 9,154,235 B2 | 10/2015 | Scherer et al. |
| 9,295,404 B2 | 3/2016 | Vano et al. |
| 9,297,691 B2 | 3/2016 | Song et al. |
| 11,206,999 B2 | 12/2021 | 'T Hooft et al. |
| 11,903,683 B2 * | 2/2024 | Cheng ............... A61B 5/686 |
| 2006/0247702 A1 | 11/2006 | Stegemann et al. |
| 2008/0255629 A1 * | 10/2008 | Jenson ............... A61N 1/056 607/19 |
| 2009/0005829 A1 | 1/2009 | Mi et al. |
| 2010/0114196 A1 | 5/2010 | Burnes et al. |
| 2011/0098533 A1 * | 4/2011 | Onoda ............... A61B 1/0051 600/117 |
| 2012/0026482 A1 | 2/2012 | Dailey |
| 2014/0131562 A1 | 5/2014 | Song et al. |
| 2014/0357997 A1 | 12/2014 | Hartmann et al. |
| 2016/0302691 A1 | 10/2016 | Feldman et al. |
| 2016/0320555 A1 | 11/2016 | Tsai et al. |
| 2016/0331980 A1 | 11/2016 | Strommer et al. |
| 2017/0196479 A1 * | 7/2017 | Liu ............... A61B 5/6852 |
| 2018/0103899 A1 | 4/2018 | Cahan et al. |
| 2018/0206752 A1 | 7/2018 | Bardy et al. |
| 2019/0030349 A1 | 1/2019 | Hoffman et al. |
| 2020/0037895 A1 | 2/2020 | Cheng et al. |

FOREIGN PATENT DOCUMENTS

| | | |
|---|---|---|
| WO | WO2014164568 A1 | 10/2014 |
| WO | WO2015164568 A1 | 10/2015 |
| WO | WO2015164571 A2 | 10/2015 |

OTHER PUBLICATIONS

De Haines, et al., "Validation of a Defibrillation Lead Ventricular Volume Measurement Compared to Three-Dimensional Echocardiography" (Abstract), Clinical Trial, Heart Rhythm, Oct. 2017.
Larson, Eric R. et al.; Analysis of the Spatial Sensitivity of Conductance / Admittance Catheter Ventricular Volume Estimation; IEEE vol. 60 Issue 8; Aug. 2013, pp. 2316-2324.
Van Rees, J.B. et al. (2011). "Inappropriate implantable cardioverter-defibrillator shocks: incidence, predictors, and impact on mortality," Journal of American College Cardiology 57:556-562.
Abbott (2022). Pulmonary Artery Pressure Monitoring: CardioMEMS™ HF System, 6 pages.
Cardiac Rhythm News (2021). "Trial underway to evaluate "modular" cardiac rhythm management system," 2 total pages.
Guo, H. et al. (2011). "Fiber optic sensors for structural health monitoring of air platforms," Sensors 11:3687-3705.
Hofer, D. et al. (2017). "Long-term incidence of inappropriate shocks in patients with implantable cardioverter defibrillators in clinical practice—an underestimated complication?" J. Interv. Card. Electrophysiol. 50:219-226.
Zhong, Y. et al. (2017). "Helical nanoribbons for ultra-narrowband photodetectors," J. Am. Chem. Soc. 139:5644-5647.
Cranch et al., "Ultra-high-sensitivity two-dimensional bend sensor", Electronic Letters, Apr. 27, 2006, vol. 42, No. 9, 2 pages.
Non-Final Office Action for corresponding U.S. Appl. No. 18/141,957, mailed Jul. 20, 2023, 9 pages.
US Notice of Allowance for corresponding U.S. Appl. No. 18/141,957, mailed Aug. 25, 2023, 9 pages.
International Search Report and Written Opinion mailed on Jul. 26, 2023, for PCT Application No. PCT/US2023/066461, filed on May 1, 2023, 7 pages.
International Search Report dated Oct. 14, 2019, corresponding to Application No. PCT/US2019/045135, 3 pages.
Written Opinion of the International Searching Authority dated Oct. 14, 2019, for PCT Application No. PCT/US2019/045135, filed on Aug. 5, 2019, 7 pages.
Second Written Opinion of the International Preliminary Examining Authority corresponding to Application No. PCT/US2019/045135, mailed Jun. 26, 2020, 7 pages.
Non-Final Office Action dated Sep. 30, 2021, for U.S. Appl. No. 16/532,112, filed Aug. 5, 2019, 16 pages.
Final Office Action dated Jul. 22, 2022, for U.S. Appl. No. 16/532,112, filed Aug. 5, 2019, 22 pages.
Non-Final Office Action dated Jan. 3, 2023, for U.S. Appl. No. 16/532,112, filed Aug. 5, 2019, 28 pages.
Final Office Action dated Jun. 20, 2023, for U.S. Appl. No. 16/532,112, filed Aug. 5, 2019, 26 pages.
Written Opinion of the International Searching Authority mailed Jul. 26, 2023, for PCT Application No. PCT/US2023/066461, filed on May 1, 2023, 5 pages.
Non-Final Office Action mailed Jul. 2, 2024, for corresponding U.S. Appl. No. 18/516,813, filed Nov. 21, 2023, 9 pages.

\* cited by examiner

NON-BAROMETRIC DETERMINATION OF HEMODYNAMIC EFFECTS OF CARDIAC ARRHYTHMIAS USING SIGNALS SENSED BY AN IMPLANTABLE DEVICE

CROSS-REFERENCE TO RELATED APPLICATIONS

This application is a continuation of U.S. patent application Ser. No. 16/532,112, filed on Aug. 5, 2019, which claims the benefit of U.S. Provisional Patent Application No. 62/714,217, filed on Aug. 3, 2018, which are hereby incorporated by reference in their entireties.

BACKGROUND

Field of the Disclosure

The present disclosure generally relates to implantable medical devices and, more particularly, to determination of hemodynamic effects of cardiac arrhythmias in a subject using signals sensed by such an implantable device.

Relevant Background

Death from heart disease (about 610,000 per year in the United States) is the leading cause of death in the U.S. and developed countries and accounts for more mortality than that from all types of cancers combined. Contrary to common belief, heart attacks are often not the immediate and direct cause of cardiac death. Rather, most cardiac deaths occur without warning (hence the term sudden cardiac death, or SCD), primarily from fatal ventricular arrhythmias (VAs) that originate from the ventricles. Fortunately, most of these SCDs due to VAs can now be prevented with the advent of implantable cardioverter/defibrillators (ICDs). ICD implantation is the most reliable therapy to reduce mortality from SCD, as validated by a large number of randomized multi-center clinical trials. Currently, accepted clinical indications for ICD implantation include: (1) primary prevention for those patients at high risk of SCD without a prior SCD event (e.g., those with a history of major heart attacks) and (2) secondary prevention for those patients who have had an SCD event, but survived. It is worthwhile to point out that the probability to survive from an SCD event without an ICD is very low (<4% if SCD occurs outside the hospital). Many of those survivors likely suffer from brain damage and fall into a vegetative state even if he or she is resuscitated.

ICDs save lives by delivering a high energy electrical shock (typically 10-35 J) to the heart to "reset" the electrical activities of the ventricles in an effort to restore normal heart rhythm. Although administering shocks saves lives, these shocks often cause severe discomfort and increase morbidity in patients. Both physical and psychological trauma may ensue. The current ICD technology depends entirely on the analysis of cardiac electric activities or electrocardiograms, i.e., electrocardiogram-based technology, to decide if the shocks should be delivered. Such technology unavoidably predisposes the patients to (1) inappropriate shocks and/or (2) premature shocks.

Inappropriate shocks refer to ICD shocks delivered when a non-fatal cardiac arrhythmia is misinterpreted as a fatal arrhythmia. A recent study (Journal of American College Cardiology 2011, 57:556-62) demonstrated that, during the follow-up period of 41±18 months, 13% of 1,544 patients with an ICD experienced at least one inappropriate shock. In addition, inappropriate shock resulted in a nearly 50% increase in the risk of all-cause mortality (hazard ratio or HR: 1.6, p=0.01, where the p value is the probability of observing and a p value of less than 0.05 is universally considered as statistically significant, i.e., as supporting evidence for the observation). Mortality risk increased with every subsequent shock, up to an HR of 3.7 after 5 inappropriate shocks. It is worth mentioning that atrial fibrillation is the most common predictor for inappropriate shocks (HR: 2.0, p<0.01), especially in patients younger than 70 years old (HR: 1.8, p=0.01). Other causes for inappropriate shocks include, but are not limited to, electrical noise and/or interference from external sources, such as a strong magnetic field or electrical interference (e.g., during certain types of welding). Noise may be due, for example, to internal sources such as fractured electrical wiring in the lead and improper or compromised internal electrical connection. Such noise and/or interference may result in false positive detection of arrhythmia and thereby lead to inappropriate ICD shocks.

Premature shocks refer to ICD shocks delivered when a potentially fatal arrhythmia is detected while the patient is still hemodynamically stable with adequate blood pressure and full consciousness. ICDs generally cannot predict the duration of an abnormal heart rhythm. For example, the abnormal heart rhythm may last for 10 beats, 20 beats, or to about half an hour or more. Currently, ICDs are configured to deliver a shock after a preset duration without any regard to a patient's hemodynamic status (e.g., the shock is delivered even if the patient still maintains an adequate blood pressure). Ideally, in such a situation, ICD shock should be withheld, and less dramatic and painless therapy, such as overdrive pacing or anti-tachycardia pacing (ATP), should be administrated.

Therefore, both types of untoward ICD shocks are shortcomings inherited in the current electrocardiogram-based ICD technology and represent the unmet need in optimal management of patients at increased risks for SCD. Minimizing inappropriate and premature shocks has become the single most important and challenging unresolved problem in today's ICD technology. Thus, it is desirable to assess the hemodynamic effects or consequences during cardiac arrhythmias immediately prior to delivery of ICD shock so that unnecessary shocking is suspended, so long as the patient is hemodynamically stable. The most intuitive approach to assess hemodynamics is to directly record intracardiac or intravascular pressure changes or a barometric signal. However, all pressure-sensing or barometric technologies depend on displacement of a mass, membrane, or diaphragm. These technologies work perfectly well in an acute setting but, in the case of a chronically implanted device, inevitable encasement of the pressure or barometric sensor by tissue fibrosis ultimately renders the sensor useless over time (e.g., weeks, months, or years) while the expected life span of the implantable devices has been expanded to 7-10 years or even longer. Currently, there is no available ICD technology to determine hemodynamics during cardiac arrhythmias such that harmful inappropriate and premature ICD shocks can be minimized or eliminated.

SUMMARY

Certain aspects of the present disclosure generally relate to determination of hemodynamic effects of cardiac arrhythmias using non-barometric signals sensed internally and processed by an implantable device. Examples of such non-barometric signals may include optical, electrical, thermal, and/or ultrasound signals.

Certain aspects of the present disclosure provide a method for determining hemodynamic stability in a subject. The method generally includes transmitting an optical signal via at least one optical fiber in a set of one or more optical fibers disposed in a heart of the subject wherein the at least one optical fiber in the set is configured to bend with mechanical movement of the heart which correlates with the contraction and relaxation of the heart during cardiac cycles; receiving a reflected portion of the optical signal via the at least one optical fiber, wherein changes in at least one parameter of the received reflected portion of the optical signal are indicative of the mechanical movement of the heart; and determining a hemodynamic stability of the subject based on the received reflected portion of the optical signal.

In an aspect, determining the hemodynamic stability of the subject comprises determining the subject is hemodynamically unstable if the changes in the at least one parameter of the received reflected portion of the optical signal are below a configurable threshold.

In an aspect, the method further includes receiving an electrocardiographic signal from one or more electrodes disposed in the subject; and detecting an arrhythmia in the subject based on the electrocardiographic signal, wherein the hemodynamic stability of the subject is determined in response to detecting the arrhythmia; and the determined hemodynamic stability is indicative of hemodynamic effects of the detected arrhythmia. For certain aspects, the electrocardiographic signal may include one or more types of noise and/or interference. In this case, detecting the arrhythmia may further include analyzing the one or more types of noise and/or interference and determining a scenario based on the noise and/or interference analysis. The scenario may indicate at least one of a presence of a magnetic field, external electrical interference, a compromised internal electrical connection, or a fractured lead, for example. For certain aspects, detecting the arrhythmia may further include analyzing the one or more types of noise and interference and detecting the arrhythmia based on the noise and interference analysis and the received reflected portion of the optical signal.

In an aspect, the reflected portion includes a portion of the optical signal reflected from within or immediately adjacent to a ventricle or ventricles of the heart.

In an aspect, the reflected portion includes a portion of the optical signal reflected by at least one optic sensor such as fiber Bragg grating sensor within the at least one optical fiber.

In an aspect, determining the hemodynamic stability of the subject includes analyzing the changes in the at least one parameter of the received reflected portion of the optical signal over a period, wherein the changes in the at least one parameter are a function of at least one of an extent of bend or a rate of bend of the at least one optical fiber; and determining whether the subject is hemodynamically stable based on the analysis.

In an aspect, the method further includes receiving a reflected portion of at least one additional optical signal via at least one additional optical fiber in the set, wherein determining the hemodynamic stability of the subject further includes analyzing changes in the at least one parameter of the received reflected portion of the at least one additional optical signal over the period; combining results of analyzing the received reflected portion of the optical signal and analyzing the received reflected portion of the at least one additional optical signal; and determining whether the subject is hemodynamically stable based on the combined results.

In an aspect, the at least one additional optical fiber may be placed within the heart of the subject or in a region within the subject that is outside the heart of the subject.

In an aspect, the method further includes receiving an electrical signal from an electrode disposed in the subject; analyzing the electrical signal over the period; combining results of analyzing the received reflected portion of the optical signal and analyzing the electrical signal; and determining whether the subject is hemodynamically stable during the detected arrhythmia based on the combined results.

In an aspect, the electrical signal is at least one of an electrocardiographic signal or an impedance signal.

In an aspect, the at least one optical fiber is disposed in at least one lead of an implantable cardioverter/defibrillator (ICD) implanted in the subject.

In an aspect, the transmitting the optical signal, the receiving the reflected portion, and the determining the hemodynamic stability of the subject are performed by an implantable device implanted in the subject, either standalone or as part of the ICD, and comprising an optical fiber or a set of optical fibers.

In an aspect, the at least one optical fiber is disposed in a ventricle of the heart.

In an aspect, the at least one parameter employed to determine hemodynamic stability includes one or more of an amplitude, a phase, a delay, or a wavelength of the received reflected portion of the optical signal or the rate of change in these parameters or the drifts in their baseline values during a cardiac cycle or over a number of cardiac cycles.

In an aspect, the method further includes automatically administering an electric shock to the heart based on the determination of the hemodynamic stability of the subject during detected arrhythmia.

In an aspect, the method further includes receiving a thermal signal indicating a temperature of at least a portion of the heart from a temperature sensor disposed in or adjacent to the heart of the subject; analyzing the changes in the at least one parameter of the received reflected portion of the optical signal and the thermal signal over a period; and combining results of analyzing the received reflected portion of the optical signal and analyzing the thermal signal, wherein determining the hemodynamic stability of the subject is based on the combined results.

In an aspect, the method further includes receiving a reflected portion of an ultrasound signal from at least one ultrasound sensor disposed in the subject; analyzing the changes in the at least one parameter of the received reflected portion of the optical signal and changes in the received reflected portion of the ultrasound signal over a period; and combining results of analyzing the received reflected portion of the optical signal and analyzing the received reflected portion of the ultrasound signal, wherein determining the hemodynamic stability of the subject is based on the combined results.

Certain aspects of the present disclosure provide an implantable system for implanting in a subject for determining hemodynamic stability of the subject. The implantable system generally includes an optical fiber or a set of optical fibers configured for placement in a heart of the subject, wherein at least one optical fiber in the set is configured to bend with a mechanical movement of the heart; at least one optical source configured to introduce an optical signal into the at least one optical fiber; at least one receiver configured to receive a reflected portion of the optical signal via the at least one optical fiber, wherein changes in at least one parameter of the received reflected portion of the optical signal are indicative of the mechanical movement of the heart; and at least one processor configured to determine a hemodynamic stability of the subject based on the received reflected portion of the optical signal.

In an aspect, the at least one processor is configured to determine the hemodynamic stability of the subject by determining the subject is hemodynamically unstable if the changes in the at least one parameter are below a configurable threshold.

In an aspect, the at least one processor is further configured to receive an electrocardiographic signal from an electrode disposed in the subject; and detect an arrhythmia in the subject based on the electrocardiographic signal, wherein the hemodynamic stability of the subject is determined in response to detecting the arrhythmia; and the determined hemodynamic stability is indicative of hemodynamic effects of the detected arrhythmia. For certain aspects, the electrocardiographic signal may include one or more types of noise and/or interference. In this case, detecting the arrhythmia may further include analyzing the one or more types of noise and/or interference and determining a scenario based on the noise and/or interference analysis. The scenario may indicate at least one of a presence of a magnetic field, external electrical interference, a compromised internal electrical connection, or a fractured lead, for example. For certain aspects, detecting the arrhythmia may further include analyzing the one or more types of noise and interference and detecting the arrhythmia based on the noise and interference analysis and the received reflected portion of the optical signal.

In an aspect, the implantable system further includes one or more leads with a plurality of electrodes configured for routing in the subject for sensing electrocardiographic signals, wherein the at least one optical fiber is disposed within a first set of leads in the one or more leads.

In an aspect, the implantable system further includes a capacitive element configured to administer an electric shock to the heart via a second set of leads in the one or more leads.

In an aspect, the first set of leads is different from the second set of leads.

In an aspect, at least one of the at least one optical source or the at least one receiver is disposed in the first set of leads.

In an aspect, the one or more leads are configured to receive the electrocardiographic signals and wherein the at least one processor is further configured to analyze the changes in the at least one parameter of the received reflected portion of the optical signal and the electrocardiographic signals over a period; and combine results of analyzing the received reflected portion of the optical signal and analyzing the electrocardiographic signals, wherein the at least one processor is configured to determine whether the subject is hemodynamically stable based on the combined results.

In an aspect, the implantable system further includes a memory coupled to the at least one processor and configured to store an electrical representation of at least one of the received reflected portion of the optical signal or the electrocardiographic signals.

In an aspect, the implantable system further includes at least one temperature sensor configured for placement in or adjacent to the heart of the subject, the at least one temperature sensor configured to measure a temperature of at least a portion of the heart, wherein a change in the temperature of the portion of the heart is indicative of the hemodynamic stability of the subject.

In an aspect, the at least one processor is further configured to analyze the changes in the at least one parameter of the received reflected portion of the optical signal and the change in the temperature over a period; and combine results of analyzing the received reflected portion of the optical signal and analyzing the temperature, wherein the at least one processor is configured to determine the hemodynamic stability of the subject based on the combined results.

In an aspect, the implantable system further includes at least one ultrasound emitter configured to transmit an ultrasound signal into the heart of the subject; and at least one ultrasound sensor configured to receive a reflected portion of the ultrasound signal, wherein a change in the received reflected portion of the ultrasound signal is indicative of the mechanical movement of the heart.

In an aspect, the at least one processor is further configured to analyze the changes in the at least one parameter of the received reflected portion of the optical signal and the received reflected portion of the ultrasound signal over a period; and combine results of analyzing the received reflected portion of the optical signal and analyzing the received reflected portion of the ultrasound signal, wherein the at least one processor is configured to determine the hemodynamic stability of the subject based on the combined results.

In an aspect, the implantable system further includes at least one optical sensor (such as a fiber Bragg grating sensor) disposed within the at least one optical fiber and having at least one characteristic range of wavelengths, the at least one fiber Bragg grating being configured to reflect at least one portion of the optical signal in the at least one characteristic range of wavelengths to generate the reflected portion of the optical signal.

In an aspect, the reflected portion includes a portion of the optical signal reflected from within or immediately adjacent to a ventricle or ventricles of the heart.

In an aspect, the at least one processor is configured to determine the hemodynamic stability of the subject by analyzing the changes in the at least one parameter of the reflected portion of the optical signal over a period, wherein the changes in the at least one parameter are a function of at least one of an extent of bend or a rate of bend of the at least one optical fiber; and determining whether the subject is hemodynamically stable based on the analysis.

In an aspect, the at least one receiver is configured to receive a reflected portion of at least one additional optical signal via at least one additional optical fiber in the set of optical fibers, wherein the at least one processor is further configured to analyze the received reflected portion of the at least one additional optical signal over the period; and combine results of analyzing the received reflected portion of the optical signal and analyzing the received reflected portion of the at least one additional optical signal, wherein the at least one processor is configured to determine the hemodynamic stability of the subject based on the combined results.

In an aspect, the at least one additional optical fiber may be placed within the heart of the subject or in a region within the subject that is outside the heart of the subject.

In an aspect, the at least one optical source includes at least one of a light-emitting diode (LED) or a laser diode, wherein the at least one receiver includes a photodetector.

In an aspect, at least one of the at least one optical source, the at least one receiver, or the at least one processor is disposed in an implantable device (e.g., an ICD) implanted in the subject.

In an aspect, a portion of the at least one optical fiber is configured for placement in or immediately adjacent to a ventricle or multiple ventricles of the heart.

In an aspect, the at least one parameter includes one or more of an amplitude, a phase, a delay, or a wavelength of the received reflected portion of the optical signal, the rate of change in these parameters, or a drift in their baseline values during a cardiac cycle or over a number of cardiac cycles (e.g., a drift or other change in a baseline amplitude, baseline phase, baseline delay, or baseline wavelength).

Certain aspects of the present disclosure provide a non-transitory computer-readable medium having instructions stored thereon that, when executed by at least one processor, cause the processor to perform operations for determining hemodynamic stability in a subject. The operations generally include transmitting an optical signal via at least one optical fiber in a set of one or more optical fibers disposed in a heart of the subject, wherein the at least one optical fiber in the set is configured to bend with a mechanical movement of the heart; receiving a reflected portion of the optical signal via the at least one optical fiber, wherein changes in at least one parameter of the received reflected portion of the optical signal are indicative of the mechanical movement of the heart; and determining a hemodynamic stability of the subject based on the received reflected portion of the optical signal.

In an aspect, determining the hemodynamic stability of the subject comprises determining the subject is hemodynamically unstable if the changes in the at least one parameter are below a configurable threshold.

In an aspect, the operations further include receiving an electrocardiographic signal from an electrode disposed in the subject and detecting an arrhythmia in the subject based on the electrocardiographic signal, wherein the hemodynamic stability of the subject is determined in response to detecting the arrhythmia and wherein the determined hemodynamic stability is indicative of hemodynamic effects of the detected arrhythmia. For certain aspects, the electrocardiographic signal may include one or more types of noise and/or interference. In this case, detecting the arrhythmia may further include analyzing the one or more types of noise and/or interference and determining a scenario based on the noise and/or interference analysis. The scenario may indicate at least one of a presence of a magnetic field, external electrical interference, a compromised internal electrical connection, or a fractured lead, for example. For certain aspects, detecting the arrhythmia may further include analyzing the one or more types of noise and interference and detecting the arrhythmia based on the noise and interference analysis and the received reflected portion of the optical signal.

In an aspect, the reflected portion includes a portion of the optical signal reflected from within or immediately adjacent to a ventricle or ventricles of the heart.

In an aspect, the reflected portion includes a portion of the optical signal reflected by at least one optical sensor (e.g., fiber Bragg grating sensor) within the at least one optical fiber.

In an aspect, determining the hemodynamic stability of the subject includes analyzing the changes in the at least one parameter of the received reflected portion of the optical signal over a period, wherein the changes in the at least one parameter are a function of at least one of an extent of bend or a rate of bend of the at least one optical fiber; and determining whether the subject is hemodynamically stable based on the analysis.

In an aspect, the operations further include receiving a reflected portion of at least one additional optical signal via at least one additional optical fiber in the set, wherein the determining includes analyzing changes in the at least one parameter of the received reflected portion of the at least one additional optical signal over the period; combining results of analyzing the received reflected portion of the optical signal and analyzing the received reflected portion of the at least one additional optical signal; and determining whether the subject is hemodynamically stable based on the combined results with enhanced discrimination of extracardiac movement artifact or noise.

In an aspect, the operations further include receiving an electrocardiographic signal from an electrode disposed in the subject; analyzing the electrocardiographic signal over the period; and combining results of analyzing the received reflected portion of the optical signal and analyzing the electrocardiographic signal, wherein determining the hemodynamic stability of the subject is based on the combined results.

In an aspect, the at least one optical fiber is disposed in at least one lead, either as a standalone lead or as an integral part of a lead for an ICD or another implantable device implanted in the subject.

In an aspect, the transmitting, the receiving, and the determining are performed by an implantable device implanted in the subject and coupled to the set of optical fibers.

In an aspect, the at least one optical fiber is disposed in a ventricle of the heart.

In an aspect, the at least one parameter includes one or more of a change in an amplitude, a phase, a delay, or a wavelength of the received reflected portion of the optical signal; the rate of change in these parameters; and/or a drift in baseline values thereof during a cardiac cycle or over a number of cardiac cycles.

In an aspect, the operations further include automatically administering an electric shock to the heart based on the determination of the hemodynamic stability of the subject during the detected arrhythmia.

In an aspect, the operations further include receiving a temperature signal indicating a temperature of at least a portion of the heart from a temperature sensor disposed in the heart of the subject; analyzing the changes in the at least one parameter of the received reflected portion of the optical signal and the temperature signal over a period; and combining results of analyzing the received reflected portion of the optical signal and analyzing the temperature signal, wherein determining the hemodynamic stability of the subject is based on the combined results.

In an aspect, the operations further include receiving a reflected portion of an ultrasound signal from an ultrasound sensor disposed in the subject; and combining results of analyzing the received reflected portion of the optical signal and the received reflected portion of the ultrasound signal, wherein determining the hemodynamic stability of the subject is based on the combined results.

Certain aspects of the present disclosure provide a method for determining hemodynamic stability of a subject. The method generally includes transmitting, using an ultrasound emitter, an ultrasound signal towards at least one anatomic reference structure within a heart of the subject over a given time period; receiving, using an ultrasound receiver, a reflected portion of the ultrasound signal over the given time period; analyzing the reflected portion of the ultrasound signal over the time period to determine changes in a distance between the ultrasound receiver and the at least one anatomic reference structure during cardiac cycles, wherein the changes are indicative of a mechanical movement of the heart; and determining the hemodynamic stability of the subject based on the mechanical movement of the heart.

In an aspect, the ultrasound emitter and the ultrasound receiver are placed in a region outside the heart within the subject.

In an aspect, the ultrasound emitter and the ultrasound receiver are integrated within an ICD implanted in the subject.

In an aspect, the ultrasound emitter and the ultrasound receiver are placed within the heart of the subject.

In an aspect, the ultrasound emitter and the ultrasound receiver are disposed in at least one lead of an ICD implanted in the subject.

In an aspect, the method further includes receiving an electrocardiographic signal from one or more electrodes disposed in the subject; and detecting an arrhythmia in the subject based on the electrocardiographic signal, wherein the hemodynamic stability of the subject is determined in response to detecting the arrhythmia; and the determined hemodynamic stability is indicative of hemodynamic effects of the detected arrhythmia. For certain aspects, the electrocardiographic signal may include one or more types of noise and/or interference. For some cases, detecting the arrhythmia may further include analyzing the one or more types of noise and/or interference and determining a scenario based on the noise and/or interference analysis. The scenario may indicate at least one of a presence of a magnetic field, external electrical interference, a compromised internal electrical connection, or a fractured lead, for example. For other cases, detecting the arrhythmia may further include analyzing the one or more types of noise and interference and detecting the arrhythmia based on the noise and interference analysis and the reflected portion of the ultrasound signal.

BRIEF DESCRIPTION OF THE DRAWINGS

So that the manner in which the above-recited features of the present disclosure can be understood in detail, a more particular description, briefly summarized above, may be had by reference to aspects, some of which are illustrated in the appended drawings. It is to be noted, however, that the appended drawings illustrate only certain typical aspects of this disclosure and are therefore not to be considered limiting of its scope, for the description may admit to other equally effective aspects.

DETAILED DESCRIPTION

Figure 1:
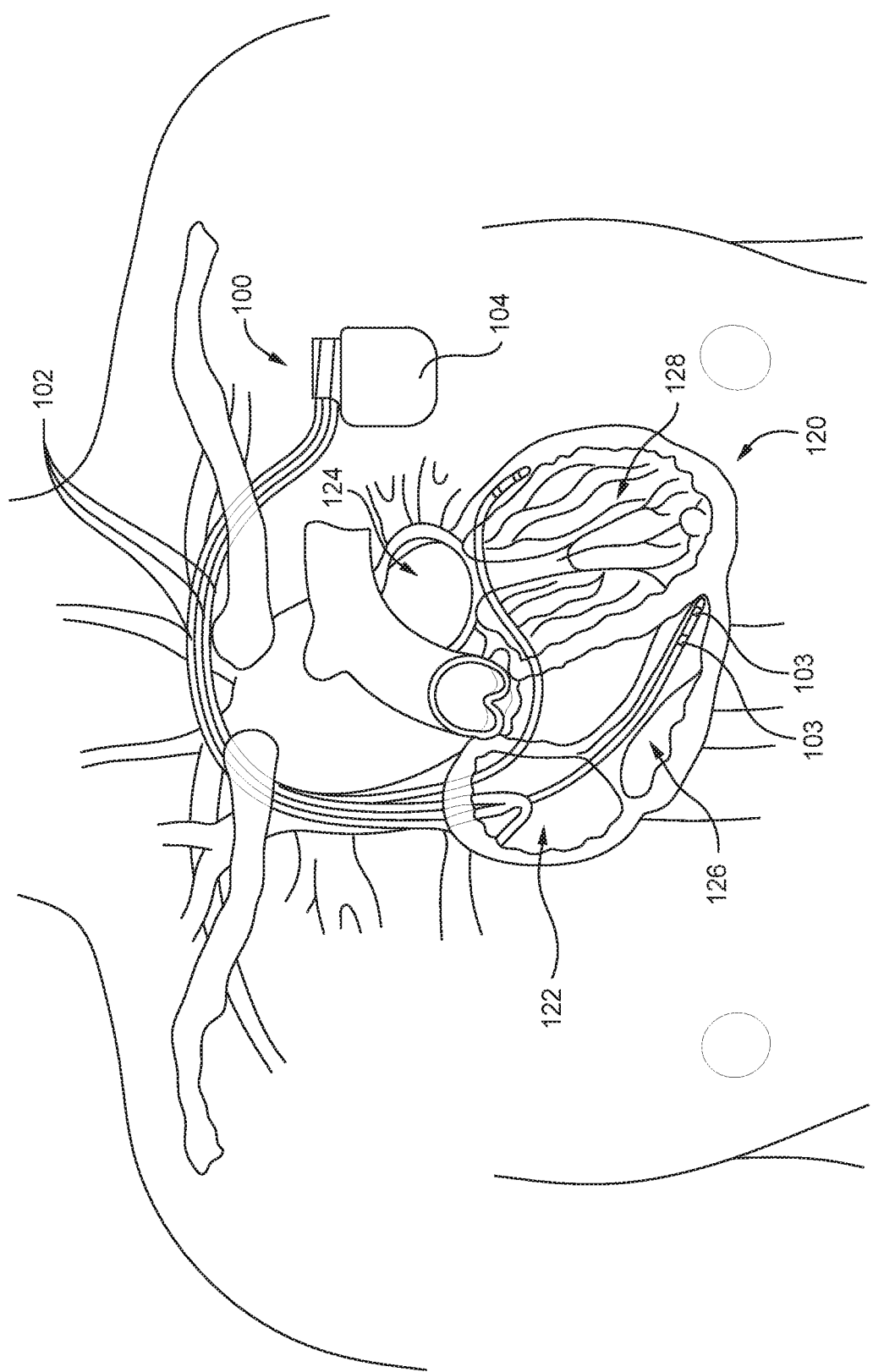
FIG. 1 illustrates an implantable cardioverter/defibrillator (ICD), as an example implantable device, in accordance with certain aspects of the present disclosure.

Certain aspects of the present disclosure provide methods and apparatus for determining hemodynamic effects of cardiac arrhythmias (e.g., fatal ventricular arrhythmia) in a subject by sensing a mechanical movement of the subject's heart using optical signals sensed by an implantable device (e.g., ICD). In certain aspects, one or more optical fibers are placed in a heart of a subject, which may extend into adjacent vascular segments of the heart, wherein the optical fibers bend as the heart contracts and relaxes (during systole and diastole). At least one parameter (e.g., amplitude, phase shift/delay, and/or wavelength) related to an optical signal passing through an optical fiber changes with the bending of the optical fiber, wherein the changes in the parameter of the optical signal are indicative of the mechanical movement of the heart. At least one processor of the implantable device, for example, in response to detecting a cardiac arrhythmia (e.g., based on electrocardiogram signals), analyzes the changes in the parameter of the optical signal and determines if the mechanical movement of the heart is sufficiently reduced to indicate hemodynamic instability in the subject during the detected cardiac arrhythmia. If such analysis indicates the subject is experiencing a fatal arrhythmia that is associated with the hemodynamic instability, the processor (e.g., in the case of an ICD) may activate the ICD to deliver an ICD shock to the subject's heart in an attempt to restore the heart's normal rhythm.

Various aspects of the disclosure are described more fully hereinafter with reference to the accompanying drawings. This disclosure may, however, be embodied in many different forms and should not be construed as limited to any specific structure or function presented throughout this disclosure. Rather, these aspects are provided so that this disclosure will be thorough and complete, and will fully convey the scope of the disclosure to those skilled in the art. Based on the teachings herein, one skilled in the art should appreciate that the scope of the disclosure is intended to cover any aspect of the disclosure disclosed herein, whether implemented independently of or combined with any other aspect of the disclosure. For example, an apparatus may be implemented or a method may be practiced using any number of the aspects set forth herein. In addition, the scope of the disclosure is intended to cover such an apparatus or method which is practiced using other structure, functionality, or structure and functionality in addition to or other than the various aspects of the disclosure set forth herein. It should be understood that any aspect of the disclosure disclosed herein may be embodied by one or more elements of a claim.

As used herein, the term "determining" encompasses a wide variety of actions. For example, "determining" may include calculating, computing, processing, deriving, investigating, looking up (e.g., looking up in a table, a database, or another data structure), ascertaining, and the like. Also, "determining" may include receiving (e.g., receiving information), accessing (e.g., accessing data in a memory), and the like. Also, "determining" may include resolving, selecting, choosing, establishing, and the like.

As used herein, the term "subject" may refer to a human or another animal, such as a pig or a dog.

Example Implantable Device

Implantable devices may include any device capable of being implanted in a subject's body. Examples include an implantable cardioverter/defibrillator (ICD), a pacemaker capable of pacing the heart at one or multiple sites, an implantable electrocardiogram electrocardiogram) device (capable of recording electrocardiogram signals), and the like.

FIG. 1 illustrates an ICD 100 with leads 102 fed through blood vessels (e.g., veins) to the heart 120 as an example of an implantable device for use with certain aspects of the present disclosure. Although the term "ICD" is used throughout this disclosure for ease of explanation, the reader is to understand that the term "ICD" may be replaced by "implantable device" throughout and that certain aspects of the present disclosure will perform the techniques described herein with any suitable implantable device capable of performing similar functions. FIG. 1 illustrates a four-chambered heart 120 with a right atrium 122, a left atrium 124, a right ventricle 126, and a left ventricle 128. Although a four-chambered heart is illustrated in FIG. 1 as a non-limiting example, aspects of the present disclosure may also apply to a heart with more or less than four chambers (e.g., a three-chambered heart), which may be due to congenital defects, for example.

The ICD 100 may comprise: (1) a generator 104 and (2) a number of leads 102, which are typically wires with multiple electrodes 103 embedded on the leads. The generator 104 may include a housing unit or "can" (typically made of titanium or another suitable metal). The housing unit may contain integrated circuits (ICs) (e.g., at least one processor and associated memory, as well as analog, digital, and/or mixed (e.g., hybrid) electronic integrated circuitries), a battery, a capacitive element (e.g., a capacitor) for storing charge and delivering a shock, and/or other hardware components (e.g., signal processing) for detecting arrhythmia and delivering ICD shocks in accordance with aspects of the present disclosure. Although three leads 102 are illustrated in FIG. 1 as a non-limiting example, aspects of the present disclosure may use more or less than three leads.

The ICD generator 104 is typically implanted subcutaneously in either the left or the right pectoral area, but may be implanted in any of various suitable areas within a subject. For example, the ICD generator 104 may alternatively be implanted subcutaneously in the upper abdomen or other regions of the body adjacent to the heart. The ICD leads 102 are connected to the generator 104 at one end and inserted into various heart chambers (e.g., the right atrium 122 and the right ventricle 126) at the other end (e.g., through the subclavian or axillary vein) or inserted into the pericardial space around the heart. At least some of the electrodes on the ICD leads 102 may be used to deliver electric current, for example, either to excite the heart muscle (similar to a pacemaker) or to stun the heart to reset a fatal VA with high electrical energy (e.g., defibrillation or ICD shocks). At least some of the electrodes on the ICD leads 102, which may be the same or different from the electrodes used for delivering current, may be used to sense the electrical activities (e.g., electrocardiogram) of the heart 120. In certain aspects, the ICD 100 may detect cardiac arrhythmias from abnormal electrical activities sensed by one or more of these electrodes 103 based on existing techniques (e.g., electrocardiogram-based technology).

In certain aspects, in addition to the ICD leads 102 or alternatively, the ICD 100 includes a set of optical fibers configured for placement in the heart 120. This set of optical fibers may extend into adjacent vascular segments of the heart, wherein at least one optical fiber in the set is configured to bend with a mechanical movement of the heart. The ICD 100 may include at least one optical source or optical transmitter (e.g., a light-emitting diode (LED) or a laser diode) configured to introduce an optical signal (e.g., light signal) into at least one optical fiber in the set. The ICD 100 may also include at least one optical receiver (e.g., a photodetector) configured to receive a reflected portion of the optical signal via the optical fiber. The optical transmitter may convert electrical signals into optical signals (e.g., light signals that may be composed of one or more frequency components across the visible and/or invisible light spectrum) under the control of at least one processor in the ICD 100 and may transmit the optical signal(s) into at least one optical fiber. The optical receiver may receive reflected portion(s) of the optical signal(s) from at least one optical fiber and convert the received optical signal(s) into electrical signal(s) (e.g., using a photodetector), which are fed back to at least one processor for analysis. In an aspect, both the optical source and the optical receiver are built into a single component (e.g., an optical transceiver) on an integrated circuit (IC) that is coupled to the optical fiber(s) at one end and to the rest of the electrical circuitry, which may include a signal processing unit and/or the at least one processor on the other end.

In certain aspects, at least one processor disposed in the generator 104 may analyze the changes in one or more parameters of the received optical signal(s). For example, the at least one processor may analyze changes in the amplitude (e.g., intensity) of a received optical signal due to changes in the angles of incidence and/or may analyze changes in the phase shift/delay of the received optical signal due to changes in lengths of the light path or may analyze changes in wavelength of a received optical signal due to the bending of the optical fiber or fibers. In an aspect, the changes in amplitude, the changes in phase shift/delay and shift in wavelength of the optical signal are indicative of changes in the amount of bending of the optical fiber(s) that is determined by the mechanical movement of the heart, due to the heart's contractile function.

In certain aspects, the at least one processor disposed in the generator 104 may determine hemodynamic stability of the subject (e.g., during a detected arrhythmia based on an electrocardiogram) according to such an analysis of the one or more parameters of the received optical signal(s) (e.g., changes in amplitude, phase shift/delay, and/or wavelength) and their correlations with direct hemodynamic measurements such as, but not limited to, blood pressure, cardiac output, cardiac filling pressure, and/or heart chamber volumes in the form of regression formula, lookup table (LUT) data, quantitative or semi-quantitative cut-off values, and/or other data of references derived either deterministically or stochastically. In this manner, the at least one processor, based on the analysis, may determine whether or not the mechanical function of the heart is sufficient to maintain hemodynamic stability during a detected cardiac arrhythmia.

The at least one processor may determine whether the heart is experiencing a potentially fatal arrhythmia (e.g., fatal ventricular arrhythmia (VA)) based on the determined hemodynamic status of the subject. In an aspect, a portion of at least one optical fiber is configured for placement in a ventricle of the heart 120 (e.g., right ventricle 126), and the at least one processor is configured to determine whether the heart is experiencing a potentially fatal VA.

The set of optical fibers may be utilized to monitor the mechanical movement of the heart continuously in certain aspects or only when an arrhythmia is detected for other aspects. The optical fibers in the set may be implemented as one or more standalone leads or incorporated as part of one or more ICD leads.

In an aspect, each optical fiber in the set physically bends with the mechanical movement of the heart, typically with the most bending or deviation at the end of systole from its resting "relaxed" position at the end of diastole. As the optical fiber bends, one or more parameters (e.g., amplitude, phase shift/delay, and/or wavelength) of the optical signal travelling through the optical fiber also change. When the heart is beating normally with a strong mechanical movement, the changes in these parameter(s) are at their maximum, indicative of normal hemodynamic stability. When the contractile function of the heart is compromised (e.g., during faster fatal ventricular tachycardia) or essentially ceases altogether (e.g., during ventricular fibrillation), the changes in one or more of these optical signal parameters may significantly diminish or become minimum as the results of fibrillatory movements or even flat-lined. In addition, the baseline values of these parameters at end diastole may change with the end-diastolic volume of the ventricles and the rates of change during cardiac cycle may also be associated with the changes in contractility and relaxation of the ventricles, An algorithm stored in the ICD memory may configure at least one processor disposed in the generator 104 to sense the changes in the received optical signal(s) and determine whether the mechanical or contractile function of the heart remains normal or compromised. In an aspect, the mechanical movement of the heart is indicative of the hemodynamic stability of the subject. If cardiac arrhythmia is detected, the algorithm may configure the at least one processor to determine whether the subject is hemodynamically unstable and, if affirmative, may trigger an ICD shock or other suitable therapy to restore normal heart rhythm. As noted above, such determination of hemodynamic stability/instability may be based on optical signals utilizing their correlations with direct hemodynamic measurements such as, but not limited to, blood pressure, cardiac output, cardiac filling pressure, and/or heart chamber volumes in the form of regression formula, lookup table data, quantitative or semi-quantitative cut-off values, and/or other data of references derived either deterministically or stochastically.

In certain aspects, since the triggering of the ICD shock is based not just on the detection of cardiac arrhythmia from electrical signals (e.g., electrocardiogram), but also on the hemodynamic stability of the subject from sensing the mechanical movement of the heart, the incidences of inappropriate or premature ICD shock of the heart may be dramatically reduced or eliminated.

In an aspect, one or more optical fibers are connected to the generator 104 at one end and inserted into various heart chambers (e.g., the right atrium 122 and the right ventricle 126) at the other end (e.g., through the subclavian or axillary vein). In an aspect, one or more optical fibers are disposed within the leads 102. In another aspect, one or more of the optical fibers may be configured as a standalone lead (e.g., does not function as an ICD or pacemaker lead).

In an aspect, an optical source and an optical receiver (or optical transceiver) are disposed within the generator 104. For example, the ICD 100 may include one or more optical transceivers to transmit and receive optical signals via one or more optical fibers. In an aspect, the optical signals may include light at any of the visible and/or invisible wavelengths (e.g., ultraviolet (UV) or infrared (IR) light).

In an aspect, an optical source and receiver (or optical transceiver) may be disposed within an ICD or pacemaker lead or a standalone lead having one or more optical fibers therein, for transmitting and receiving optical signals via the one or more optical fibers. In this case, electrical lines (e.g., wires) may connect the optical transceiver with the generator 104 to provide electrical power to the transceiver (e.g., from a battery housed in the can).

In an aspect, an optical receiver or transceiver receives a portion of a transmitted optical signal reflected from within the same or different optical fiber(s) that may be routed to and partially disposed in a heart of a subject and that may extend into adjacent vascular segments of the heart. In an aspect, at least one optical fiber may have one or more light-reflecting mechanism(s), such as a fiber Bragg grating (FBG), configured with at least one characteristic wavelength, and/or another optically reflective component (e.g., a fiber mirror), disposed within the optical fiber. The receiver or the transceiver may receive the portion of the optical signal reflected by at least one of the light-reflecting mechanisms (e.g., FBG).

In certain aspects, at least one processor of the generator 104 may be configured to combine results the from analyzing electrical signals (e.g., electrocardiogram) from the electrodes and the results from analyzing the optical signals, for a more accurate determination of a potentially fatal arrhythmia. For example, the at least one processor may detect a cardiac arrhythmia based on the electrocardiogram signals and, in response, may further determine hemodynamic stability of the subject based on the optical signals. The at least one processor may decide to deliver a shock to the heart if the subject is determined to be hemodynamically unstable. Thus, the at least one processor may determine the hemodynamic effects of a cardiac arrhythmia (e.g., detected based on the electrical signals) based on the optical signals, and may decide to deliver a shock to the heart based on the determination of hemodynamic instability of the heart in the presence of the detected cardiac arrhythmia.

In certain aspects, multiple optical fibers are routed to and partially disposed in the heart and may extend into adjacent vascular segments of the heart to provide redundancy and to differentiate the effects of mechanical movement of the heart from the effects of external or extracardiac movements. In this case, at least one processor of the generator 104 may be configured to receive multiple optical signals from the multiple optical fibers and combine the results of analyzing the multiple optical signals in an attempt to detect the hemodynamic stability of the heart. In this context, one or more additional optical fibers/sensors may be placed within different regions the heart to monitor the mechanical movements of these different regions. Results from these different optical fibers/sensors may be combined to determine the hemodynamic stability of the heart. In an aspect, multiple optical sensors may be integrated into one or more ICD leads traversing the heart at different places on the ICD leads. Additionally or alternatively, one or more additional optical fibers/sensors may be placed in a region outside the heart within the subject to monitor-non cardiac body movements. These non-cardiac body movements determined based on these additional optical sensors may be cancelled out in order to determine cardiac movements.

In certain aspects, the ICD 100 includes one or more temperature sensors configured for placement in the heart 120 of the subject. The temperature sensor measures a temperature of at least a portion of the heart, wherein a change in the temperature of the portion of the heart may be indicative of diminished blood flow during cardiac arrhythmias, which in turn may be indicative of abnormal heart rhythm. In certain aspects, at least one processor of the generator 104 is configured to analyze the change in the temperature within the heart over a period and combine the thermal data with the results of analyzing the received optical signal(s) over the same period. The at least one processor may be configured to determine whether or not the heart is functioning normally, and consequently, whether or not the subject is hemodynamically stable, based on the combined optical and thermal results and utilizing correlations between the optical and thermal signals with direct hemodynamic measurements such as, but not limited to, blood pressure, cardiac output, cardiac filling pressure, and/or heart chamber volumes in the form of regression formula, lookup table data, quantitative or semi-quantitative cut-off values, and/or other data of references derived either deterministically or stochastically.

In certain aspects, changes in the temperature of the heart may be measured based on changes in one or more parameters of an optical signal being conveyed via an optical fiber routed to and partially disposed in the heart. In an aspect, the temperature measurement through the optical fiber placed in the heart may change with the change in temperature of the heart, consequently changing the wavelength/frequency of the optical signal conveyed via the optical fiber. Thus, the changes in wavelength/frequency of the optical signal are indicative of the temperature changes of the heart. A photodetector receiving the optical signal may detect the changes in the wavelength/frequency of the received optical signal and may determine temperature changes of the heart based on the detected changes in the wavelength/frequency of the optical signal.

In certain aspects, the ICD 100 includes at least one ultrasound emitter (e.g., a piezoelectric transducer) configured to transmit an ultrasound signal toward at least one anatomic reference structure within the heart 120 (e.g., the intraventricular septum) and/or surrounding the heart (e.g., the sternum), and at least one ultrasound sensor configured to receive a reflected portion of the ultrasound signal. For certain aspects, the ultrasound emitter and the ultrasound sensor may be physically integrated together into an ultrasound transceiver. The reflected ultrasound signals may be analyzed to determine the changes in the distance between the transceiver and the at least one anatomic reference during heartbeats or cardiac cycles, which may be indicative of the mechanical movement of the heart.

In an aspect, the ultrasound emitter and/or the ultrasound receiver (or transceiver) are configured for attachment to a lead and may be disposed as a standalone lead or be incorporated into an ICD lead 102.

Figure 2:
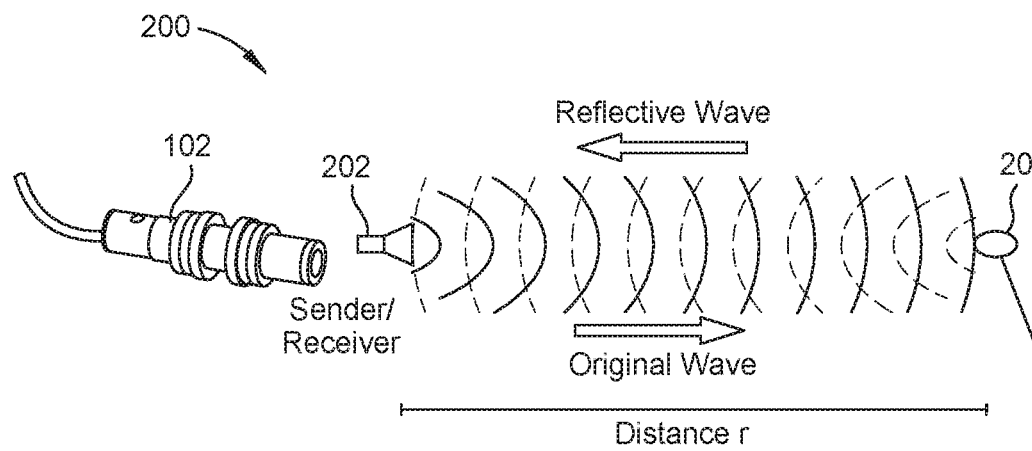
FIG. 2 illustrates an example ultrasound transceiver configuration in which the ultrasound transceiver is built into an ICD lead, in accordance with certain aspects of the present disclosure.

FIG. 2 illustrates an example ultrasound transceiver configuration 200 in which the ultrasound transceiver is built into an ICD lead 102, in accordance with certain aspects of the present disclosure. One or more ultrasound transceivers 202 may be built into the ICD lead 102 and may be configured to transmit ultrasound signals and detect portions of the transmitted ultrasound signals reflected from various structures distinct ultrasound characteristics 204 within the heart (e.g., the ventricular free walls and the intraventricular septum) and/or outside the heart (e.g., the subject's sternum). In certain aspects, multiple ultrasound emitters (or transceivers) may be embedded into the ICD lead 102. In this case, each emitter (or transceiver) may be configured to transmit ultrasound signals in a different direction within the heart of the subject. For instance, the at least one transceiver may be mounted on the tip of the lead with the ultrasound beam directed forward or conversely one or more transceivers may be mounted on the side of the lead with the ultrasound beam directed laterally. In an aspect a combination forward and lateral configurations may be used, i.e., one or more ultrasound transceivers may be mounted on the tip and one or more ultrasound transceivers may be mounted laterally. In an aspect, data from reflected ultrasound signals received from different directions from within the heart may be combined to generate a more accurate representation of the heart movements. In an aspect, the collected data may be used to generate a real-time three-dimensional model of the heart to help monitor the mechanical movement of the heart in real time.

In this example configuration, electrical lines (e.g., wires) may connect the transceiver(s) 202 with the generator 104 to provide electrical power to the transceiver (e.g., from a battery housed in the can). Additionally, the transceiver may send data collected from receiving reflected ultrasound signals to the generator 104 by transmitting the data on additional data lines running between the transceiver and the generator 104 or by wirelessly transmitting the data to the generator 104.

Data relating to reflected ultrasound signals may also be retrieved from the ICD, for example, via telemetry (e.g., a telemetry wand) and be analyzed by an external processing system (e.g., comprising one or more processors outside of the subject's body), for example for generating the real-time model of the heart. Such a processing system may also be part of a remote centralized patient monitoring center communicating with the ICD through radio frequency (RF) (e.g., Bluetooth®) or other remote communication technologies.

In an aspect, the ultrasound emitter and/or the ultrasound receiver (or transceiver) are configured for placement in a suitable region in the subject external to the heart 120 of the subject. For example, the ultrasound transceiver may be integrated into the generator 104 of the ICD 100 or may be implanted in a suitable region in the subject as a separate device (i.e., separate from the generator 104). For example, the transceiver may be implanted subcutaneously in either the left or the right pectoral area, or in any of various other suitable areas within the subject, such as in the upper abdomen or other regions of the body adjacent to the heart. When implanted as a separate device, electrical lines (e.g., wires) may connect the ultrasound transceiver with the generator 104 to provide electrical power to the transceiver (e.g., from a battery housed in the can). Further, the transceiver may send data collected from receiving reflected ultrasound signals to the generator 104 by transmitting the data on additional data lines running between the transceiver and the generator 104 or by wirelessly transmitting the data to the generator 104.

When used in the external configuration, the ultrasound transceiver may be configured to transmit ultrasound signals in the general direction of the heart. In an aspect, the signals reflected off the ICD leads 102 placed within the heart may be more pronounced as compared to signals reflected off heart tissue. Since the ICD leads 102 are at least partially constructed out of metal, the leads will have stronger reflections as compared to heart tissue. In an aspect, since the ICD leads 102 move with the mechanical movements of the heart, heart movements may be tracked by tracking movements of ICD leads 102.

Figure 3:
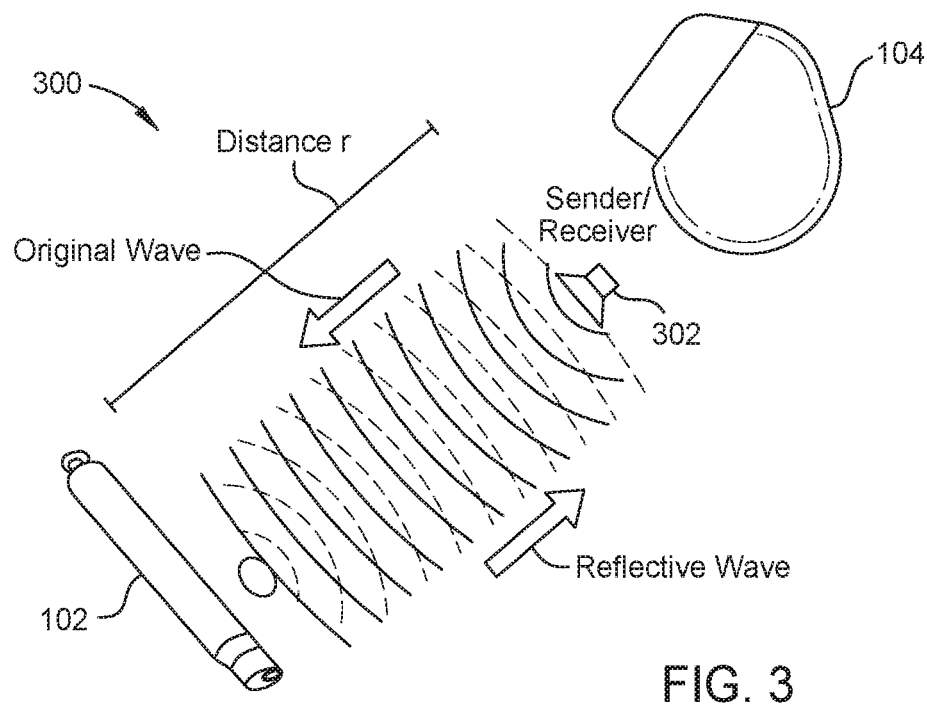
FIG. 3 illustrates an example ultrasound transceiver configuration in which one or more ultrasound transceivers are built into an ICD generator, in accordance with certain aspects of the present disclosure.

FIG. 3 illustrates an example ultrasound transceiver configuration 300 in which the ultrasound transceiver is built into an ICD generator 104, in accordance with certain aspects of the present disclosure. The ultrasound transceiver 302 is integrated into the ICD generator housing. The transceiver 302 transmits ultrasound signals in the general direction of the heart and detects signals reflected off different heart surfaces, structures within the heart and off at least some portions of the ICD lead 102 placed within the heart. Since the reflections from the ICD lead 102 are much stronger and distinguishable from reflections from other organic heart tissue, the movements of the ICD leads may be easily tracked. The received ultrasound signals may be analyzed (e.g., by one or more processors) to track the movements of the ICD lead 102 and determine heart movements based on the tracked movements of the ICD lead 102. For instance, the ultrasound signal may be analyzed to determine the changes in the distance between the transceiver and at least one anatomic reference during heartbeats or cardiac cycles, which may be indicative of the mechanical movements of the heart. In an aspect, the surface of the ultrasound transceiver may be shaped as flat, concave or convex to optimize the detection of the ICD lead.

An advantage of this approach is that stray ultrasound signals reflected off other organs such as lungs may not affect the determination as the reflections from the ICD lead 102 will be significantly different from other reflections.

In an aspect, at least a portion of the lead movements may be caused by the subject's general body movements. In an aspect, one or more accelerometers may be used to detect other body movements of the subject, and these body movements may be cancelled out from the determination of the lead movements resulting from heart movements.

In certain aspects, at least one processor in the generator 104 is configured to analyze the received ultrasound signals over a period and combine the ultrasound data with the results of analyzing the received optical signals over the same period. The at least one processor may be configured to determine whether or not the heart is functioning normally, and consequently, whether or not the subject is hemodynamically stable, based on the combined optical and ultrasound results and utilizing correlations between the optical and ultrasound signals with direct hemodynamic measurements such as, but not limited to, blood pressure, cardiac output, cardiac filling pressure, and/or heart chamber volumes in the form of regression formula, lookup table data, quantitative or semi-quantitative cut-off values, and/or other data of references derived either deterministically or stochastically.

In certain aspects, the ICD 100 may be connected to electrodes embedded in a standalone lead or incorporated into the ICD lead 102 for measuring impedance changes within at least one chamber of the heart (e.g., right ventricle 126) during a heartbeat or cardiac cycle. In an aspect, the impedance within the ventricles changes with a change in the volume of the heart as a result of the mechanical contraction and relaxation of the heart. Thus, changes in the impedance are indicative of the mechanical movement of the heart. In certain aspects, at least one processor in the generator 104 is configured to analyze the received impedance signals over a period and combine the results with the results of analyzing the received optical signals over the same period. The at least one processor is configured to determine whether or not the heart is functioning normally, and consequently, whether or not the subject is hemodynamically stable, based on the combined optical and impedance results and utilizing correlations between the impedance and optical signals with direct hemodynamic measurements such as, but not limited to, blood pressure, cardiac output, cardiac filling pressure, and/or heart chamber volumes in the form of regression formula, lookup table data, quantitative or semi-quantitative cut-off values, and/or other data of references derived either deterministically or stochastically.

In certain aspects, the at least one processor may be configured to determine the hemodynamic stability of the subject based independently on the optical signals, thermal signals, ultrasound signals, or impedance signals, or on a combination of two or more of these aforementioned signals and to utilize correlations therebetween with direct hemodynamic measurements such as, but not limited to, blood pressure, cardiac output, cardiac filling pressure, and/or heart chamber volumes in the form of regression formula, lookup table (LUT) data, quantitative or semi-quantitative cut-off values, and/or other data of references derived either deterministically or stochastically.

In certain aspects, changes in the mechanical movement of the heart may be detected using radio frequency (RF) signals. For example, the electrodes 103 may be configured to transmit RF signals within the heart and receive RF signals reflected from within the heart (e.g., reflected from the heart tissue/walls). The at least one processor may analyze the reflected RF signals and determine whether or not the heart is mechanically compromised, and in turn, determine hemodynamic stability of the subject. For certain aspects, such use of RF signals may be combined with any of the other techniques described herein, such as use of electrocardiogram, optical, thermal, ultrasound, and/or impedance signals, for determining hemodynamic stability.

In certain aspects, the ICD itself (more specifically, the processor within the ICD) or another implantable device (e.g., a second device in addition to the ICD) may perform a quantitative analysis of at least one of the optical signals, the electrocardiogram signals, thermal signals, impedance signals, or the ultrasound signals sensed and/or stored by the implantable device(s) to determine whether the heart is experiencing a fatal arrhythmia. Alternatively, data pertaining to at least one of the received optical signals, the electrocardiogram signals, thermal signals, impedance signals, or the ultrasound signals (e.g., stored and/or currently sensed signals) may be retrieved, for example, via telemetry (e.g., a telemetry wand) and be analyzed by an external processing system (e.g., comprising one or more processors outside of the subject's body). Such a processing system may also be part of a remote centralized patient monitoring center communicating with the ICD through radio frequency (RF) (e.g., Bluetooth®) or other remote communication technologies.

In certain aspects, the at least one processor may be configured to determine whether the heart is experiencing arrhythmia based on the electrocardiogram signals, and determine the hemodynamic effects of the detected arrhythmia based on one or a combination of the optical signals, thermal signals, impedance signals, or the ultrasound signals sensed and/or stored by the implantable device(s) to determine whether the detected arrhythmia is fatal in nature. The at least one processor may be configured to decide to administer an ICD shock to the heart if it is determined that the subject is hemodynamically unstable, for example, by utilizing correlations with direct hemodynamic measurements such as, but not limited to, blood pressure, cardiac output, cardiac filling pressure, and/or heart chamber volumes in the forms of regression formula, lookup table data, quantitative or semi-quantitative cut-off values, and other data of references derived either deterministically or stochastically.

Figure 4:
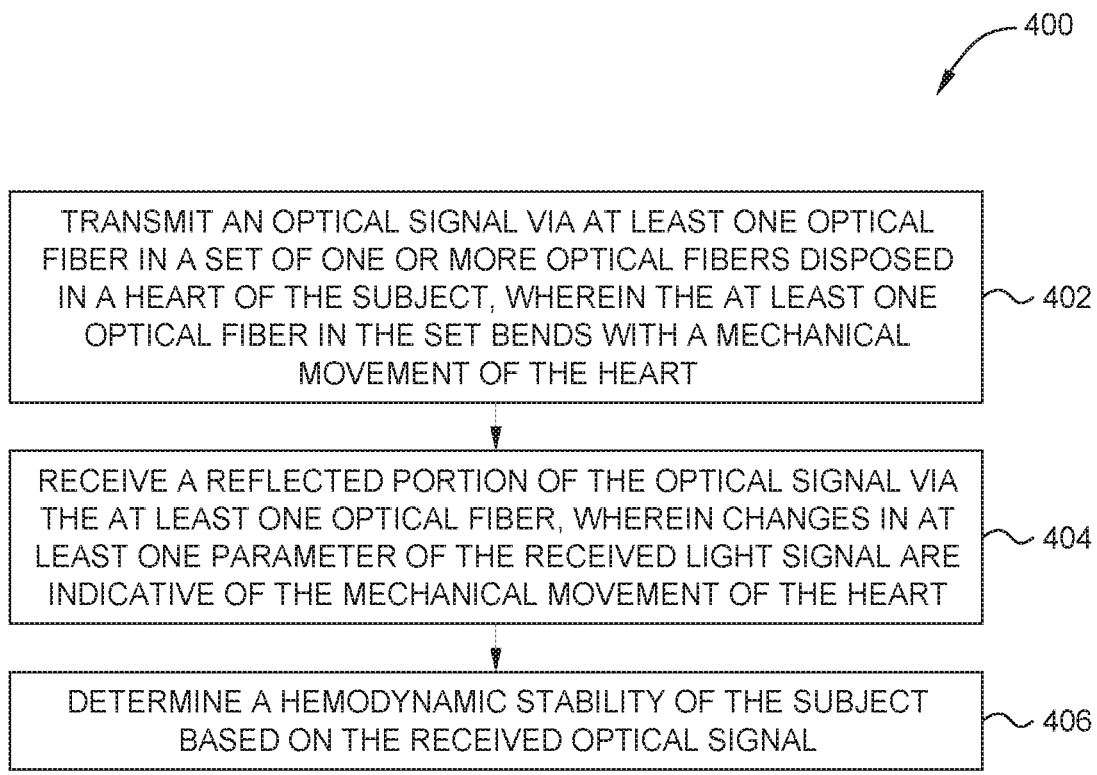
FIG. 4 is a flow diagram of example operations for determining hemodynamic stability in a subject, in accordance with certain aspects of the present disclosure.

FIG. 4 is a flow diagram of example operations 400 for determining hemodynamic stability in a subject (e.g., a human patient or animal), in accordance with certain aspects of the present disclosure. The operations 400 may be performed by an implantable device, such as ICD 100. For certain aspects, at least some of the operations 400 may be performed by any suitable system with a telemetry device (e.g., through radio frequency (RF), such as Bluetooth®, or other wireless communication technologies) and one more processors coupled to the telemetry device and configured to read signals received from an implantable device via the telemetry device. For example, the system may include a programmer that communicates with an ICD through wireless communication methods, such as Bluetooth® technology, other RF signals, or other telecommunication technologies. The system may also be part of a centralized remote patient monitoring/management center through RF (e.g., Bluetooth®) or other wireless communication technologies The operations 400 begin, at block 402, by transmitting an optical signal via at least one optical fiber in a set of one or more optical fibers partially disposed in a heart of the subject, that may extend into adjacent vascular segments of the heart, wherein the at least one optical fiber in the set is configured to bend with a mechanical movement of the heart.

At block 404, a reflected portion of the optical signal is received via the at least one optical fiber, wherein changes in at least one parameter of the received reflected portion of the optical signal are indicative of the mechanical movement of the heart. In an aspect, the at least one parameter includes one or more of an amplitude, a phase, or a delay of the optical signal.

At block 406, a hemodynamic stability of the subject is determined based on the received reflected portion of the optical signal.

In an aspect, determining the hemodynamic stability of the subject includes determining the subject is hemodynamically unstable if the mechanical movement of the heart is below a configurable threshold (e.g., over a period).

In an aspect, an electrocardiogram signal (also known as an electrocardiographic signal) is sensed by one or more electrodes disposed in the subject, and arrhythmia is detected in the subject based on the electrocardiogram signal. The hemodynamic stability of the subject is determined in response to detecting the arrhythmia, wherein the determined hemodynamic stability is indicative of the hemodynamic effects of the detected arrhythmia.

In certain aspects, for determining the hemodynamic stability of the subject, changes in the at least one parameter of the received reflected portion of the optical signal are analyzed over a period, wherein the changes in the at least one parameter are a function of at least one of an extent of bending or a rate of bending (e.g., as reflected by a first derivative of the received reflected portion of the optical signal) of the at least one optical fiber. The determination of whether the subject is hemodynamically stable is based on the analysis. In an aspect, the changes in the at least one parameter are indicative of the mechanical movement of the heart, and thus, analyzing these changes indicates if the mechanical or contractile function of the heart is behaving normally or is compromised. In an aspect, if the analysis of the optical signal indicates that the mechanical movement of the heart is sufficiently compromised to indicate hemodynamic instability, it may be determined that an ICD shock is to be delivered to the heart in an effort to restore the heart's normal rhythm.

In certain aspects, the ICD first detects a potentially fatal arrhythmia based on electrical signals (e.g., internal electrocardiogram) only. However, the ICD does not decide to deliver an ICD shock at this time based only on the detected arrhythmia. Instead, in response to detecting the arrhythmia, the ICD monitors and analyzes the optical signals as described above in an attempt to determine the hemodynamic effects of the detected arrhythmia. The ICD decides to deliver a shock to the heart of the subject upon detecting hemodynamic instability in the subject in response to the detected arrhythmia. For example, if hemodynamic instability is detected indicating a significant compromise in the mechanical function of the heart sufficient to cause hypotension, an ICD may decide to deliver the shock in an attempt to restore the normal rhythm of the heart. On the other hand, if hemodynamic stability is determined indicating the reduction of the mechanical function of the heart is not sufficient to cause hypotension, an ICD shock may be withheld so that inappropriate and/or premature ICD shocks are minimized or avoided.

In certain aspects, operations 400 further include receiving a reflected portion of one or more additional optical signal(s) via one or more additional optical fiber(s) in the set. The changes in the at least one parameter of the additional received optical signal(s) are analyzed over the same time period, and results of analyzing the received first optical signal and analyzing the received additional optical signal are combined. The determination of whether the subject is hemodynamically stable is based on the combined results, which may increase the sensitivity and specificity of hemodynamic determination, especially in the presence of external or extracardiac mechanical movement or noise. This is because cardiac movements will result in differential effects in the optical fibers placed in different locations in the heart or along the different sides of the same ICD lead, whereas extracardiac movements tend to result in similar effects on all intracardially-placed optical fibers.

In certain aspects, the operations 400 further include receiving electrocardiogram signals and other electrical signals such as impedance measurements from an electrode or electrodes disposed in the subject (e.g., heart of the subject) and analyzing the electrocardiogram signal and other electrical signals such as impedance measurements over the same time period. The results of analyzing the received reflected portion of the optical signal and analyzing the electrocardiogram and electrical signals are combined. In this case, the determination of whether the subject is hemodynamically stable during a cardiac arrhythmia may be based on the combined results.

In certain aspects, the operations 400 further include receiving a thermal signal indicating changes in temperature of at least a portion of the heart from a temperature sensor disposed in the heart of the subject. The thermal signal is analyzed over the same time period and results of the analyzing are combined with the results of analyzing the received reflected portion of the optical signal. In this case, the determination of whether the subject is hemodynamically stable may be based on the combined results.

In certain aspects, the operations 400 further include receiving a reflected portion of an ultrasound signal from an ultrasound sensor disposed in the subject and analyzing the received reflected portion of the ultrasound signal over the same time period. The results of analyzing the received reflected portion of the ultrasound signal are combined with the results of analyzing the received optical signal. In this case, the determination of whether the subject is hemodynamically stable may be based on the combined results.

In an aspect, the reflected portion of the optical signal includes a portion of the optical signal reflected from within a portion (e.g., ventricle) of the heart. In an aspect, the reflected portion of the optical signal includes a portion of the optical signal reflected by at least one light-reflecting mechanism, such as a fiber Bragg grating, within the at least one optical fiber.

According to certain aspects, the implantable device is capable of administering an electric shock to a heart of the subject, for example, based on the determination the heart is experiencing a potentially fatal arrhythmia (e.g., fatal ventricular arrhythmia) and that the subject is hemodynamically unstable. In this case, the implantable device may include an implantable cardioverter/defibrillator (ICD). For other aspects, the implantable device includes a pacemaker, an internal electrocardiogram (recording) device, or other implantable medical device that may activate an audible warning and/or transmit an alarm signal remotely through RF (e.g., Bluetooth®) or other wireless communication technologies to an external device or to a centralized patient monitoring/management center.

According to certain aspects, the implantable device may have multiple leads with a plurality of electrodes for sensing the internal electrocardiogram signals and measuring impedance. For certain aspects, the implantable device comprises at least two leads with at least four electrodes.

In an aspect, at least one optical fiber in the set of optical fibers is disposed in an ICD lead or as a separate lead (also referred to herein as a standalone lead) implanted in the subject.

In an aspect, at least one optical fiber in the set is at least partially disposed in a ventricle of the heart of the subject. In this case, the determining whether the heart is experiencing a fatal arrhythmia includes determining whether the subject is hemodynamically stable while the heart is experiencing ventricular arrhythmia (VA).

According to certain aspects, the subject is a human patient. For other aspects, the subject may be a pig or a dog, for example.

According to certain aspects, the implantable device may store the internal electrocardiogram signals (and derivatives thereof), which may be processed in either digital or analog forms, during single or multiple VA events that can originate from single or multiple ventricular sites for comparison, analysis, and localization of the VA(s) by medical personnel during device interrogation.

According to certain aspects, electrical noise and/or interference sensed by electrodes implanted in the subject may be falsely diagnosed as part of the "detected arrhythmia." The implanted electrodes may include, for example, one or more electrodes 103 in one or more leads 102 of the ICD 100 or other implanted device. For example, the electrodes may pick up external interference (e.g., from strong magnetic fields or certain types of welding) and/or internal noise from fractured leads or compromised internal electrical connections. Certain aspects of the present disclosure may be capable of distinguishing between such types of noise and true arrhythmia based upon signals that are immune to electrical noise and interference, including the non-barometric signals described herein, such as optical, thermal, and/or ultrasound signals. Distinguishing between the types of noise and true arrhythmia may be performed, for example, by comparing one or more features of the electrical signals with one or more features of at least one non-barometric signal. Example features of the signals that may be analyzed include frequency-domain content (e.g., the frequency value(s), bandwidth(s), and/or other characteristics of the frequency spectrum) and/or time-domain content (e.g., amplitude and/or temporal characteristics) for the non-barometric, noise, and/or interference signals. Distinguishing between the types of noise and true arrhythmia may be essentially based on: (1) lack of significant changes from their respective baselines, (2) lack of hemodynamic compromises, or (3) both in the non-barometric signals (e.g., optical, thermal and/or ultrasound signals) that are expected to occur during true arrhythmia. The optical, thermal, and/or ultrasound signals, for example, may exclude such electrical noises from being misdiagnosed as arrhythmia based on simultaneous analysis of one or more of these non-barometric signals and the electrocardiographic signal.

Figure 5:
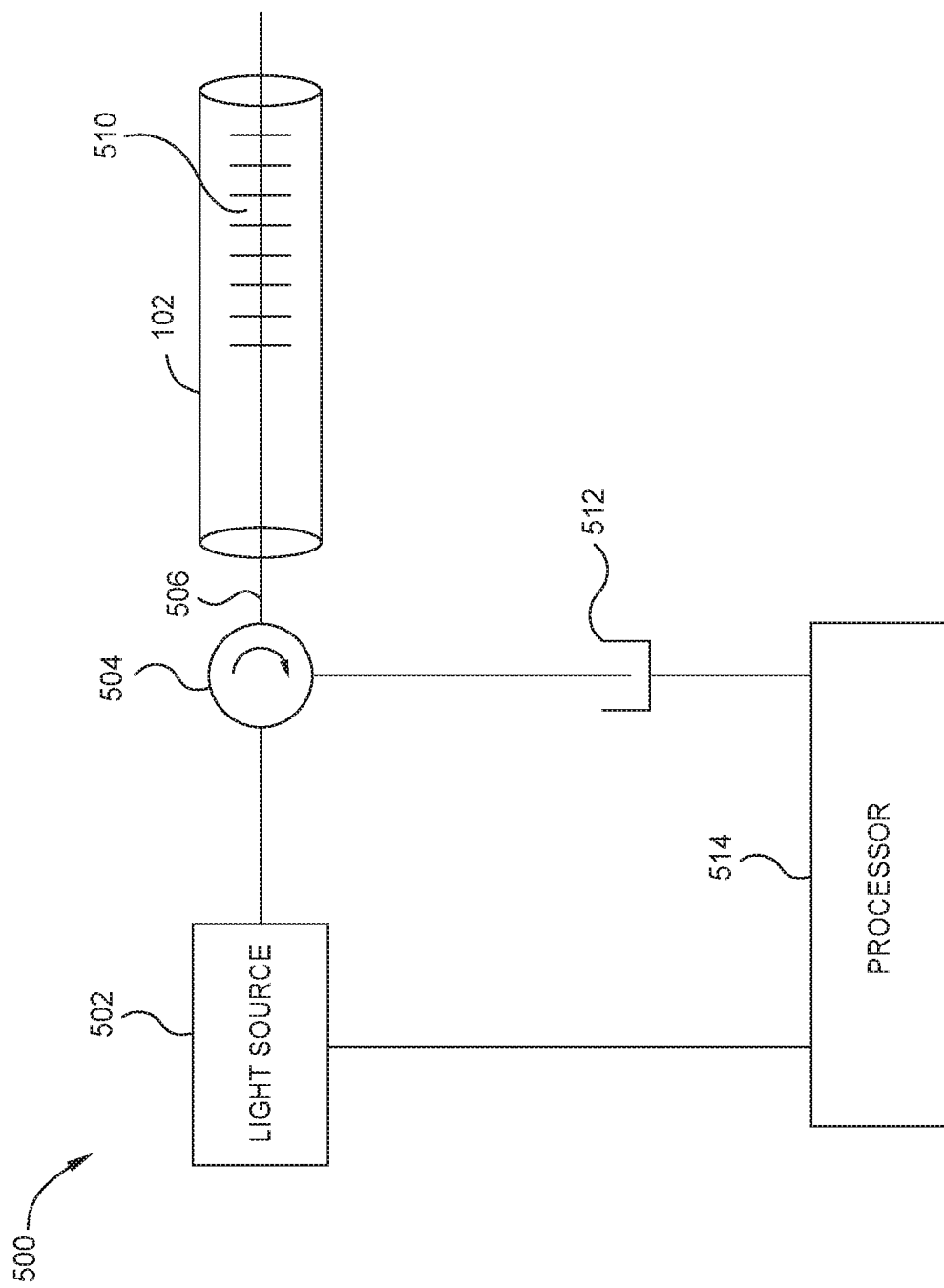
FIG. 5 illustrates a portion of an implantable system for determining hemodynamic stability in a subject with optical signal, in accordance with certain aspects of the present disclosure.

FIG. 5 illustrates a portion of an implantable system 500 for determining hemodynamic instability during detected arrhythmias, in accordance with certain aspects of the present disclosure.

As shown, the implantable system 500 includes an optical source 502 that outputs an optical signal (e.g., a light signal in the visible and/or invisible light spectrum). As noted above, the optical source 502 may include a light-emitting diode (LED) or a laser diode. The optical signal produced by the optical source 502 may be coupled to an optical fiber 506 via an optical circulator 504. The optical fiber 506 is configured to be at least partially placed in the heart of a subject. A fiber Bragg grating 510 may be provided close to a distal segment of the optical fiber 506 for placement in the heart of the subject. The fiber Bragg grating 510 is configured to reflect at least a portion of the optical signal transmitted by the optical source 502 at a characteristic range of wavelengths (also known as the Bragg wavelength). Light reflections from the fiber Bragg grating 510 pass back into the optical circulator 504 and to the optical sensor 512, such as a photodetector. The sensor 512 converts the Bragg wavelength reflections into electrical signals having amplitudes that may also reflect the energy loss of the reflected optical signal, as it passes through the optical fiber(s), which is a function of angles of incidence determined by the amount of bending of the optical fiber(s). The sensor 512 may also detect the time delay in the reflected optical signal, as the signal passes through the optical fiber(s), which is a function of the lengths of paths determined by the amount of bending of the optical fiber(s). Alternatively, an optically reflective mirror or other optical reflector other than a fiber Bragg grating may be placed at the end of the optical fiber to reflect the optical signal.

As shown, the optical source 502 and the optical sensor 512 are coupled to a processor 514 that controls the optical output from the optical source 502, and receives and processes electrical signals received from the optical sensor 512 to determine if the mechanical or contractile function of the subject is normal or preserved, and consequently, whether the subject is hemodynamically stable.

In an aspect, as shown in FIG. 5, the optical fiber 506 may be embedded in an ICD lead 102 of an ICD 100 (e.g., as shown in FIG. 1) or as a standalone lead. In an aspect, the optical source 502, the optical sensor 512, the optical circulator 504, and the processor 514 along with an associated memory may be housed in a generator unit (e.g., generator 104 shown in FIG. 1) of the ICD 100 as discrete components or as part of an application-specific integrated circuit (ASIC).

Figure 6A:
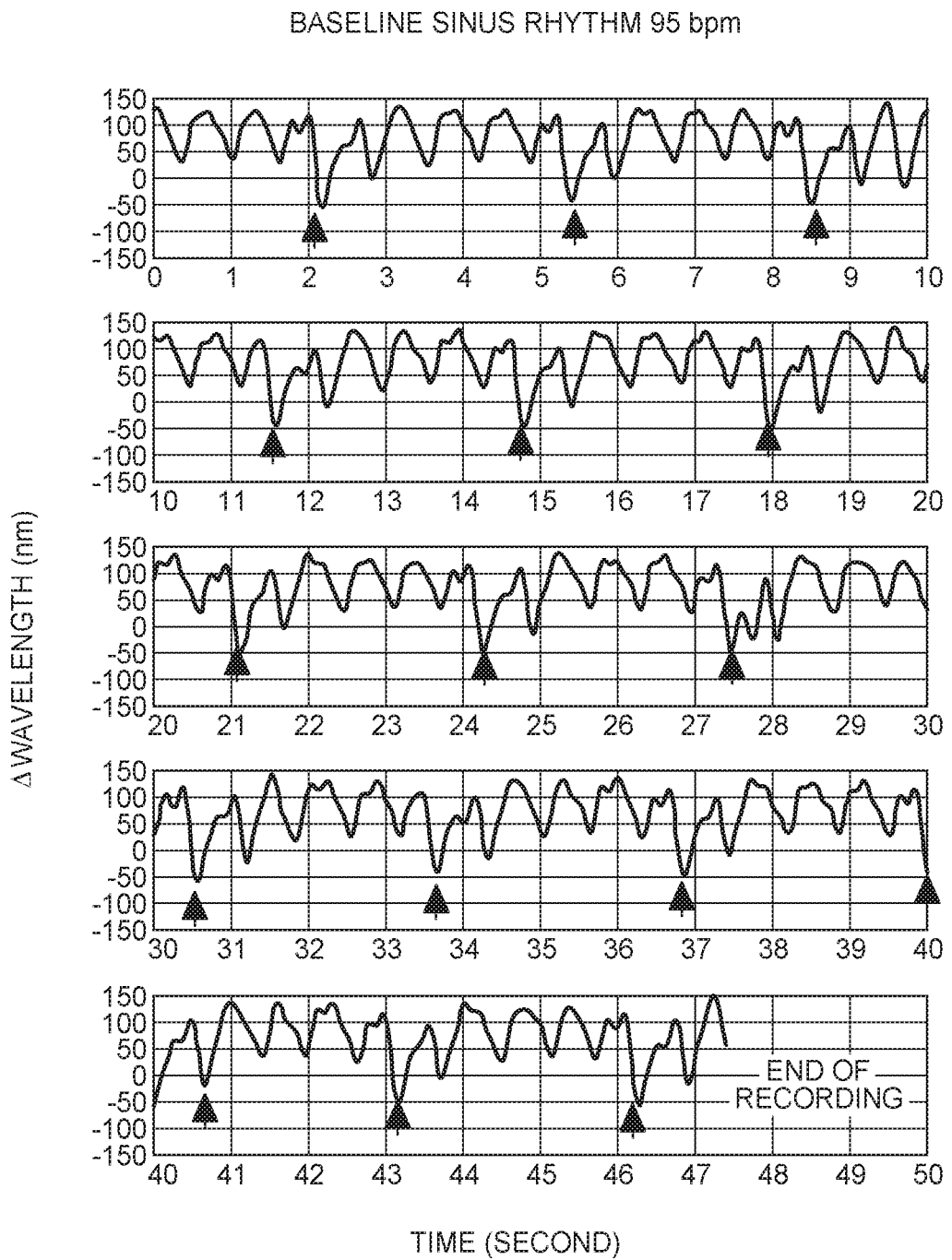
FIGS. 6A, 6B, and 6C illustrate example recorded optical signals during a representative experiment involving monitoring the mechanical movements of a subject's heart based on the optical signals, in accordance with certain aspects of the present disclosure.
Figure 6B:
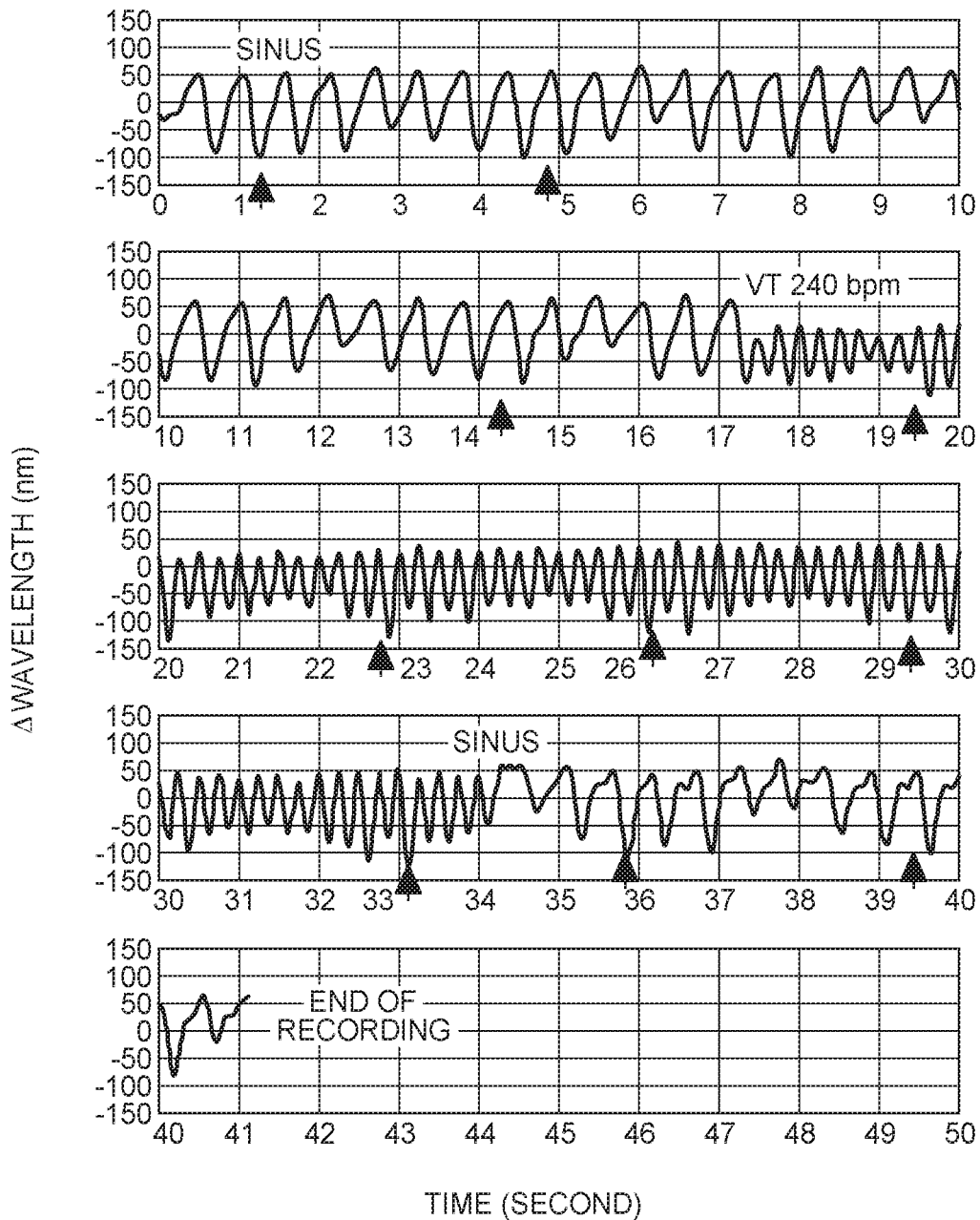
Figure 6C:
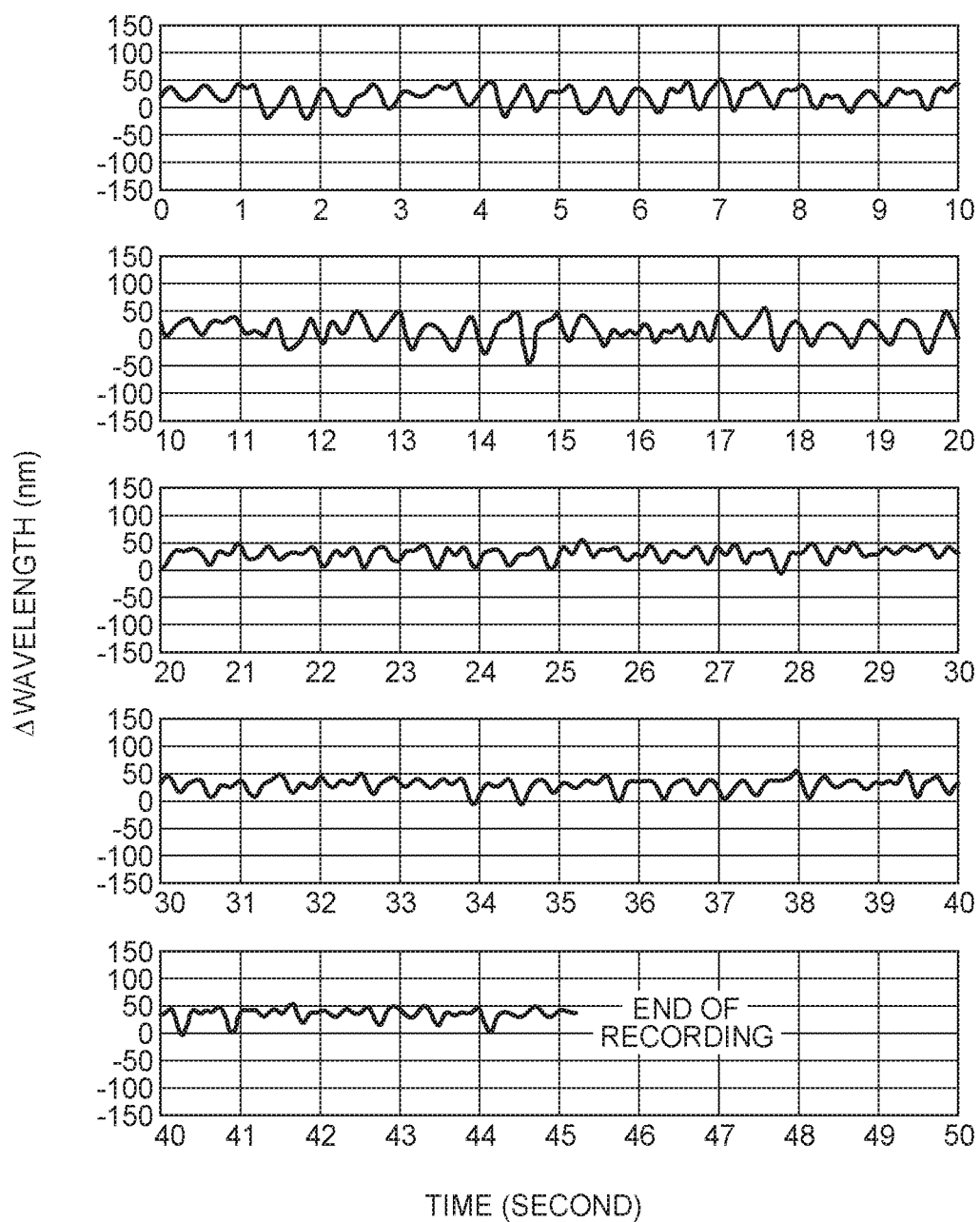

FIGS. 6A, 6B, and 6C illustrate example recorded optical signals during a representative experiment involving monitoring the mechanical movements of a subject's heart based on the optical signals, in accordance with certain aspects of the present disclosure. Each of FIGS. 6A, 6B, and 6C show changes in the wavelength of the monitored optical signal over time.

FIG. 6A illustrates a baseline sinus rhythm of 95 beats per minute (bpm). The optical signal is correlated with the movement of the ventricles during cardiac cycle and is affected by respiration, as well, which can be identified and isolated from cardiac signals based upon their respective spectral and temporal characteristics.

FIG. 6B illustrates effects of ventricular tachycardia (VT). Ventricular pacing (v-pacing) is used to simulate the VT originating from the left ventricle. As may be observed from the plots of FIG. 6B, a diminished magnitude of change in wavelength is noted during VT (e.g., 240 bpm), reflecting the diminished contractile function of the ventricle and, hence, its mechanical movement. A slight but noticeable downward drift in the optical signal is also noted during VT, indicating a change (enlargement) of the dimensions or volume of the ventricle during successive cardiac cycles. As shown in the bottom two plots of FIG. 6B, the optical signal did not recover immediately after restoration of the sinus rhythm, which is consistent with usual residual hemodynamic effects of sustained VT.

FIG. 6C illustrates effects of ventricular fibrillation. The ventricular fibrillation is induced with rapid ventricular pacing. As may be seen from the plots of FIG. 6C, the optical signal is further diminished during ventricular fibrillation, which is consistent with completely compromised cardiac contractile function.

Figure 7:
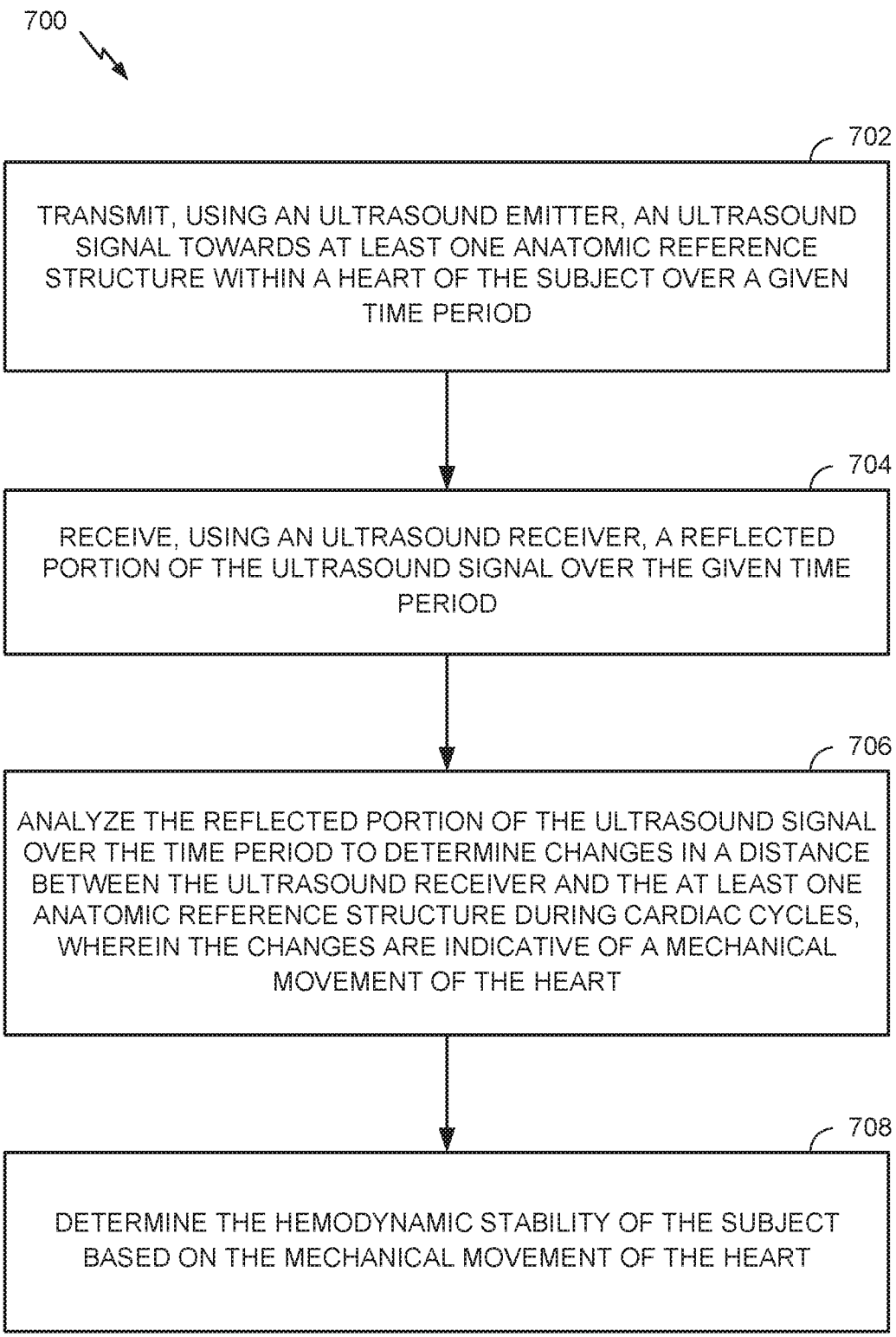
FIG. 7 illustrates example operations for determining hemodynamic stability in a subject using ultrasound signals, in accordance with certain aspects of the present disclosure.

FIG. 7 illustrates example operations 700 for determining hemodynamic stability in a subject using ultrasound signals, in accordance with certain aspects of the present disclosure.

Operations 700 begin, at block 702, by transmitting, using an ultrasound emitter, an ultrasound signal towards at least one anatomic reference structure within a heart of the subject over a given time period.

At block 704, an ultrasound receiver receives a reflected portion of the ultrasound signal over the given time period.

At block 706, the reflected portion of the ultrasound signal is analyzed over the time period to determine changes in a distance between the ultrasound receiver and the at least one anatomic reference structure during cardiac cycles, wherein the changes are indicative of a mechanical movement of the heart.

At block 708, the hemodynamic stability of the subject is determined based on the mechanical movement of the heart.

In an aspect, the ultrasound emitter and the ultrasound receiver are placed in a region outside the heart within the subject. For example, the ultrasound emitter and the ultrasound receiver may be integrated within an ICD implanted in the subject.

In an aspect, the ultrasound emitter and the ultrasound receiver are placed within the heart of the subject. For example, the ultrasound emitter and the ultrasound receiver may be disposed in at least one lead of an ICD implanted in the subject.

Any of the operations described above, such as the operations 400, may be included as instructions in a computer-readable medium for execution by a processing system. The (non-transitory) computer-readable medium may comprise any suitable memory or other storage device for storing instructions, such as read-only memory (ROM), random access memory (RAM), flash memory (e.g., USB flash drive), an electrically erasable programmable ROM (EEPROM), a compact disc ROM (CD-ROM), a floppy disk, or a digital versatile disc ROM (DVD-ROM).

The methods disclosed herein comprise one or more steps or actions for achieving the described method. The method steps and/or actions may be interchanged with one another without departing from the scope of the claims. In other words, unless a specific order of steps or actions is specified, the order and/or use of specific steps and/or actions may be modified without departing from the scope of the claims.

As used herein (including the claims that follow), a phrase referring to "at least one of" a list of items refers to any combination of those items, including single members. As an example, "at least one of: x, y, and z" is intended to cover: x, y, z, x-y, x-z, y-z, x-y-z, and any combination thereof (e.g., x-y-y and x-x-y-z).

While the foregoing is directed to certain aspects of the present disclosure, other and further aspects may be devised without departing from the basic scope thereof, and the scope thereof is determined by the claims that follow.

The invention claimed is:

1. An implantable system for implanting in a subject for determining hemodynamic stability of the subject, comprising:
at least one optical fiber configured for placement in at least one of a heart of the subject or adjacent to a ventricle of the heart, wherein the at least one optical fiber comprises at least one fiber Bragg grating (FBG) and is configured to bend with contraction and relaxation of the heart;
at least one optical source configured to introduce an optical signal into the at least one optical fiber;
at least one receiver configured to receive a reflected portion of the optical signal via the at least one FBG of the at least one optical fiber; and
at least one processor configured to:
analyze a change in at least one parameter of the received reflected portion of the optical signal, wherein the change in the at least one parameter includes a Bragg wavelength shift, and wherein the Bragg wavelength shift is indicative of an amount of bending of the at least one optical fiber due to contraction and relaxation of the heart; and
determine the hemodynamic stability of the subject based on the Bragg wavelength shift.

2. The implantable system of claim 1, further comprising one or more leads, wherein the at least one optical fiber is disposed within a first lead of the one or more leads.

3. The implantable system of claim 1, wherein at least one of the at least one optical source, the at least one receiver, or the at least one processor is disposed in an implantable device.

4. The implantable system of claim 3, wherein the implantable device includes a generator and wherein the at least one processor is disposed within the generator.

5. The implantable system of claim 3, wherein the implantable device includes a generator, and wherein the at least one optical source and the at least one receiver are disposed within the generator.

6. The implantable system of claim 3, wherein the at least one processor is disposed in another device.

7. The implantable system of claim 6, wherein the other device is disposed external to the subject.

8. The implantable system of claim 6, wherein the other device is configured for implantation in the subject.

9. The implantable system of claim 1, wherein the at least one receiver is configured to receive a reflected portion of at least one additional optical signal via at least one additional optical fiber, wherein the at least one processor is configured to:
analyze a change in the at least one parameter of the received reflected portion of the at least one additional optical signal; and
combine results of analyzing the received reflected portion of the optical signal and analyzing the received reflected portion of the at least one additional optical signal, wherein the at least one processor is configured to determine the hemodynamic stability of the subject based on the combined results.

10. The implantable system of claim 9, wherein the at least one additional optical fiber is disposed outside the heart and wherein the combined results are indicative of the hemodynamic stability of the subject in the presence of non-cardiac body movements.

11. The implantable system of claim 1, wherein the at least one optical fiber is positioned in a first region of the heart to monitor a mechanical movement of the first region, the system further comprising at least one additional optical fiber positioned in a second region of the heart to monitor a mechanical movement of the second region.

12. The implantable system of claim 1, wherein the at least one processor is further configured to:
   receive electrocardiographic signals from an electrode disposed in the subject;
   analyze the electrocardiographic signals; and
   combine results of analyzing the received reflected portion of the optical signal and analyzing the electrocardiographic signals, wherein the at least one processor is configured to determine whether the subject is hemodynamically stable based on the combined results.

13. A non-transitory computer-readable medium having instructions stored thereon that, when executed by at least one processor, cause the at least one processor to perform operations for determining a hemodynamic stability of a subject, the operations comprising:
   transmitting an optical signal via at least one optical fiber in a set of one or more optical fibers disposed in at least one of a heart of the subject or adjacent to a ventricle of the heart, wherein the at least one optical fiber in the set is configured to bend with contraction and relaxation of the heart;
   receiving a reflected portion of the optical signal via the at least one optical fiber, wherein a change in at least one parameter of the received reflected portion of the optical signal is indicative of an amount of bending of the at least one optical fiber due to contraction and relaxation of the heart, wherein the change in the at least one parameter includes a Bragg wavelength shift; and
   determining the hemodynamic stability of the subject based on the Bragg wavelength shift.

14. The implantable system of claim 1, wherein the at least one optical fiber is disposed within a chamber of the heart or an adjacent vascular segment of the heart.

* * * * *